(12) United States Patent
Dukan et al.

(10) Patent No.: US 9,493,809 B2
(45) Date of Patent: Nov. 15, 2016

(54) METHOD FOR SPECIFICALLY LABELING LIVING BACTERIA

(71) Applicant: CENTRE NATIONAL DE LA RECHERCHE SCIENTIFIQUE (CNRS), Paris (FR)

(72) Inventors: Sam Dukan, Marseilles (FR); Audrey Dumont, Marseilles (FR); Monzer Awwad, Cachan (FR); Annie Malleron, Marcoussis (FR); Boris Vauzeilles, Sceaux (FR)

(73) Assignees: CENTRE NATIONAL DE LA RECHERCHE SCIENTIFIQUE (CNRS), Paris (FR); UNIVERSITE PARIS SUD, Orsay (FR)

( * ) Notice: Subject to any disclaimer, the term of this patent is extended or adjusted under 35 U.S.C. 154(b) by 13 days.

(21) Appl. No.: 14/372,652

(22) PCT Filed: Jan. 16, 2013

(86) PCT No.: PCT/EP2013/050712
§ 371 (c)(1),
(2) Date: Jul. 16, 2014

(87) PCT Pub. No.: WO2013/107759
PCT Pub. Date: Jul. 25, 2013

(65) Prior Publication Data
US 2014/0363817 A1 Dec. 11, 2014

(30) Foreign Application Priority Data

Jan. 18, 2012 (EP) .................................... 12151622

(51) Int. Cl.
*C12Q 1/04* (2006.01)
*G01N 33/58* (2006.01)
*C12Q 1/10* (2006.01)

(52) U.S. Cl.
CPC . *C12Q 1/10* (2013.01); *C12Q 1/04* (2013.01); *G01N 33/582* (2013.01)

(58) Field of Classification Search
None
See application file for complete search history.

(56) References Cited

U.S. PATENT DOCUMENTS

| 9,057,093 B2 * | 6/2015 | Fovet | C12Q 1/04 |
| 9,181,204 B2 * | 11/2015 | Leibl | C07D 249/06 |
| 9,181,575 B2 * | 11/2015 | Fovet | C12Q 1/06 |
| 2008/0268468 A1 | 10/2008 | Wong et al. | |
| 2014/0363817 A1 * | 12/2014 | Dukan | C12Q 1/04 435/6.11 |

FOREIGN PATENT DOCUMENTS

| EP | 2868750 | * | 5/2015 |
| WO | 2010010983 A1 | | 1/2010 |
| WO | WO 2010/136209 A1 | * | 12/2010 |
| WO | WO 2013/107759 A1 | * | 7/2013 |
| WO | WO 2015/063173 A1 | * | 5/2015 |

OTHER PUBLICATIONS

Mas Pons et al, 248$^{th}$ ACS National Meeting and Exposition, Aug. 10-14, 2014, Meeting abstract.*
Tao et al, Glycobiology vol. 18 No. 10 pp. 761-769, 2008.*
Zeng et al, Nature Methods | vol. 6 No. 3 | Mar. 2009 | 207-209.*
International Search Report mailed Apr. 5, 2013 corresponding to International Patent Application PCT/EP2013/050712.
Gross H J et al: "Enzymatic introduction of a fluorescent sialic acid into oligosaccharide chains of glycoproteins", European Journal of Biochemistry, vol. 177, No. 3, 1988, pp. 583-589.
Barr T A et al.:"Quantum dots decorated with pathogen associated molecular patterns as fluorescent synthetic pathogen models.", Molecular Biosystems, vol. 6, No. 9, 2010, pp. 1572-1575.
Yi W et al: "Remodeling bacterial polysaccharides by metabolic pathway engineering", PNAS, vol. 106, No. 11, 2009, pp. 4207-4212.

* cited by examiner

*Primary Examiner* — Nita M Minnifield
(74) *Attorney, Agent, or Firm* — Ladas & Parry LLP

(57) ABSTRACT

The present invention concerns a method for labeling specifically living bacteria of a given category in a sample, the method including: a) incubating said bacteria of said sample with at least one analog of a monosaccharide compound, and b) contacting the bacteria with a labeling molecule having a second reactive group.

29 Claims, 5 Drawing Sheets

METHOD FOR SPECIFICALLY LABELING LIVING BACTERIA

This application is a 371 of PCT/EP2013/050712, filed on Jan. 16, 2013, which claims priority to European Application No. 12151622.3, filed Jan. 18, 2012.

The present invention concerns a method for specifically labeling and more particularly for specifically detecting living bacteria in a sample comprising bacteria.

The traditional methods for detecting living bacteria involve the culture of the bacteria and their numbering by visualization of colonies on a solid medium. Such methods are not rapid as the culturing may take a longtime. Moreover, these methods are necessarily restricted to the detection of cultivable bacteria and not living bacteria. Indeed, the quantification thereof is not reliable because it has been shown that some bacteria are killed due to the stress of the culture on solid medium. Indeed, using plate counts, microbiologists have made one important hypothesis, in a sense that they assumed that this method had no deleterious effects on bacteria. However, and since 1950s it was reported that apparently dead cells could be reactivated, when scavengers (such as pyruvate, catalase, superoxide dismutase . . . ) of reactive oxygen species, naturally produced during aerobic respiration, were added on agar plates [40-48]. For instance, various stresses like starvation, HOCl, heat shock and desiccation, may leave cells in a vulnerable physiological state in which atmospheric oxygen, during the recovery period, increases the toxic effect of the primary stressor.

In order to overcome these limitations, a number of indirect non-culture-based methods have been proposed to assess bacterial viability, all of which have also advantages and disadvantages. Hence, there is no method that has been agreed upon as suitable in all cases. These methods assess viability by one of two criteria, demonstration of metabolic activity or maintenance of cellular structures.

Before the use of fluorescence technology, methods which have been used as indications of cellular metabolic activity include the use of micro-autoradiography [25] as well as inducible enzyme activity [26] as an indicator of de novo protein synthesis, the direct viable count method (DVC) [27] which is based on the enlargement of cells upon addition of nutrient, and the reduction of tetrazolium salts as an indication of an active electron transport chain [28]. There are, however, disadvantages associated with the use of these methods. DVC and tetrazolium salt reduction assays require nutrient addition [28, 29] and are thus dependent upon the ability of the organism to respond to the nutrient supplied. Measurements of respiration also have their drawbacks. A range of factors has been shown to affect formazan deposit formation from tetrazolium salt reduction [29], and a report showed that the tetrazolium salt, 5-cyano-2,3-ditolyl tetrazolium chloride, inhibits bacterial metabolism [30].

Cell viability assays have also been developed based on the staining of cells with Fluorochromes. These methods assess viability by the maintenance of stable cellular structures. Acridine orange direct counts [31] and 4P, 6-diamidino-2-phenylindole staining [32] have been used as an indication of the maintenance of intact nucleic acids. Rhodamine 123 has been used extensively as an indicator of membrane potential and with the development of flow cytometry, there has been a surge of methods for characterization of the physiological status of the cells [33]. Permeability of these dyes may be a problem in some organisms. More recently, some new assays have been used to assess bacterial viability, these characterize some aspect of metabolic activity (like esterase activity followed by the Chem-Chrome V6 fluorescent probe) [34], of cellular integrity (like membrane integrity—BacLight Kit), membrane potential, intracellular pH [35] and finally ATP [36]. Finally, a new approach has been developed since 2002 involving messenger RNA-based detection of viable bacterial pathogens and real-time PCR quantification of pathogens [37].

Using methods allowing the detection of viable cell at a single cell level, microbiologists have made one important hypothesis, in a sense that they assume that these cells will over time be able to re-grow. However, some authors have proposed that this observation is a consequence of cellular deterioration and that viable but non-cultivable cells are on their way to death [40, 49].

By consequence, it can be expected that the number of apparently viable cells over-estimate the number of truly alive cells (cultivable, namely able to divide/multiply over time).

While many of these methods have the above mentioned limitations, it is furthermore apparent that non-living bacteria maintain certain characteristics of viable cells which are involved in these methods, such as the enzymatic activity. Accordingly, these methods involve a great number of false positive detection and quantification and the number of bacteria detected and quantified is not sufficiently reliable.

The goal of the present invention was to provide a new improved indirect non-culture-based method for specifically detecting living bacteria, especially overcoming the above mentioned drawbacks and providing a more reliable detection and quantification of the accurate number of cultivable bacteria.

Metabolic glycan labeling [1] has recently emerged as a very powerful tool to study cell surface glycans, with applications ranging from their imaging in living multicellular organisms such as zebra fish or mice to identification of metastasis associated cell-surface sialoglycoproteins [2]. This strategy relies on the assimilation by the cellular biosynthetic machinery of a modified monosaccharide bearing a bio orthogonal chemical reporter. Metabolic incorporation of this reporter into glycans can be further visualized by chemical ligation with a label such as a fluorescent probe. Somewhat surprisingly, studies have mainly focused on the labeling of vertebrate glycans [3] using derivatives of common monosaccharides such as N-acetyl neuraminic acid or its N-acetyl mannosamine precursor, N-acetyl glucosamine, N-acetyl galactosamine and fucose.

Despite a much higher degree of diversity in their monosaccharidic building blocks and an essential role in bacterium-host interactions and bacterial virulence, bacterial polysaccharides have been poorly explored for in vivo structural modifications. Bacteria are divided into Gram positive and Gram negative bacteria. Whereas Gram positive bacteria are surrounded by a peptidoglycan cell wall, Gram negative bacteria are covered by a dense layer of Lipopolysaccharides (LPS) embedded in their outer membrane, and which are involved in the structural integrity of the cell and are often considered as pathogenicity determinants.

A repetitive glycan polymer contained within a LPS is referred to as the O antigen, O polysaccharide, or O side-chain of the bacteria. The O antigen is attached to the core oligosaccharide, and comprises the outermost domain of the LPS molecule. The composition of the O chain varies from strain to strain. For example, there are over 160 different O antigen structures produced by different E. coli strains. O antigen is exposed on the very outer surface of the bacterial cell. The Core domain always contains an oligosaccharide component that attaches directly to lipid A and commonly contains sugars such as heptose and 3-deoxy-D-mannooctulosonic Acid (also known as KDO, ketodeoxyoctonic acid).

Lipopolysaccharide (LPS) is one of the most important cell-surface polysaccharides, as it plays a key structural role in outer membrane integrity, as well as being an important mediator of host-pathogen interactions.

Other bacterial glycans of the outer membrane of the bacteria comprise capsular polysaccharides (CPS), which are linear and consist of repeating subunits of mono-saccharides, and glycoproteins.

Glycoproteins have been shown to be important for adhesion and invasion during bacterial infection.

Although LPS appears as an interesting target for specific and well-defined glycan metabolic labeling in Gram negative bacteria, attempts have still been limited to the introduction of modified L-fucose derivatives into a purposely genetically engineered *Escherichia coli* strain [4]. This last approach presents however some limitations, since:

(a) L-fucose is not generally present within the LPS of all Gram negative bacteria, but is found in the O-antigens of specific strains [5], (b) Free L-fucose is not an intermediate in the normal *E. coli* "de novo" pathway, and should therefore not be directly activatable into a nucleotide-sugar donor [6] without the introduction by genetic engineering of an alternative pathway, known as "salvage pathway", into the organism of interest (metabolic pathway engineering), and (c) Once activated in the form of GDP-Fuc, the modified L-fucose analogue might, following the reverse de novo pathway, be transformed into GDP-Man and potentially further metabolized into various other compounds, the chemical reporter being now susceptible to spread through other pathways of the sugar metabolism (or beyond).

As the above mentioned LPS labeling on bacteria required therefore genetic modification of the bacteria, it could not be used in a method of detecting any living bacteria in a tested sample according to the present invention.

According to the present invention it has been investigated whether other sugars could be used as a target for glycan metabolic modification of at least a given category of bacteria without requiring genetic modification of the said bacteria, taking advantage of the fact that metabolic modification would then be an evidence of viability of the bacteria.

The method of the present invention therefore comprises essentially detecting viable bacteria in labeling the bacterial membranes thereof via metabolic modification of membrane glycans thereof, especially the Lipopolysaccharides, by incorporating into their membrane glycans, especially their LPS, a modified sugar component bearing a bio orthogonal chemical reporter, thus decorating the cell surface and enabling the detection thereof with a chemistry reaction, especially click chemistry reaction, allowing further detecting of the chemical reporter, in an overall rapid process as schematically shown on FIG. 2B.

According to the present invention it has been found that modified sugars comprising ulosonic acid or ulosonate residue are particularly advantageous in that such residues can be found in glycans of the bacterial membrane, especially LPS of all of the Gram negative bacteria, and moreover they can be directly assimilated in the form into which they will be incorporated in the said glycans, especially the LPS of Gram negative bacteria, while most of the other sugars of the LPS come from a different monosaccharidic precursor.

Ulosonic acids (also called ketoaldonic acids, or aldulosonic acids) are monosaccharides of the ketose family, presenting a ketone function at C-2, and a carboxylic acid at C-1. Octulosonic and nonulosonic acids are found in diverse natural glycans, including different forms of bacterial glycans (especially LPS, CPS, glycoproteins). The biosynthetic pathway leading to the elaboration of these glycans generally involves the free ulosonic acid as an intermediate, which is then directly activated in the form of a CMP-sugar donor. This is in contrast with many other monosaccharides which are often biosynthesized directly in the form of nucleotide diphosphate-sugar donors from a small set of primary activated donors of simple monosaccharides.

The present invention provides a method for labeling specifically living bacteria of a given category of bacteria in a sample comprising bacteria, in incorporating a first reactive chemical group bound to the glycans of the outer membrane of said living bacteria.

More accurately, the present invention provides a method for specifically labeling living bacteria of a given category of bacteria in a sample comprising bacteria, the method comprising the steps of:

a) incubating said bacteria of said sample with at least one analog of a monosaccharide compound, said monosaccharide being an endogenous monosaccharide residue of glycans of the outer membrane of such given category of bacteria, the said endogenous monosaccharide residue comprising an ulosonic acid or ulosonate salt residue, the said analog of a monosaccharide compound being a modified monosaccharide substituted at a given position by a first reactive chemical group capable to react with a second reactive group of a labeling molecule, the said given position being preferably a position which comprises a free group in the said endogenous monosaccharide residue incorporated within said glycans of the outer membrane of the bacteria, b) contacting said bacteria with a said labeling molecule comprising a said second reactive group, for generating the reaction of said first reactive group of said analog residue incorporated within said glycans of the outer membrane of said living bacteria with said second reactive group of said labeling molecule.

Living bacteria comprise bacteria capable of multiplying as well as viable bacteria not capable to multiply. As most of the sanitary regulations refer to the numbering of bacteria capable to multiply, especially capable to multiply on a solid growth medium, advantageously, the present invention provides more particularly a method for labeling specifically bacteria capable of multiplying wherein said bacteria are incubated in a culture medium in (liquid medium) or on (solid medium) which said bacteria are capable to multiply.

Preferably, the method of the present invention comprises the further step of:

c) detecting living bacteria in detecting whether said bacteria comprise labeling molecule bound to the glycans of their outer membrane and/or immobilizing living bacteria bearing said labeling molecule, onto a solid substrate.

The said detecting step c) can be carried out in a liquid medium or on a solid substrate.

More particularly, said labeling molecule is a detectable molecule comprising a detectable substance or capable to react or to be bound to a detectable substance or said labeling molecule is a first molecule bearing a said second reactive group, said first molecule being capable to react or to be bound to a second molecule and/or to a solid substrate, preferably said second molecule comprising a detectable substance and/or said second molecule being bound to a said solid substrate.

In a first embodiment, said labeling molecule can be a detectable molecule, namely a molecule consisting in or bearing a detectable substance, namely a substance capable to be detected such as a fluorochrome or luminescent substance or an enzyme such as peroxidase, said enzyme being more particularly detected after reacting with a coreactant.

In a further particular embodiment, useful for isolating living bacteria, the said labeling molecule can be bound to a solid substrate when carrying out step b).

In a further particular embodiment, said labeling molecule is molecule which is a first ligand or first binding protein bearing a said second reactive group and in step c) said living bacteria coupled to said first ligand or first binding protein is detected and/or immobilized by contacting said first ligand or first binding protein with a second molecule which is a second ligand or second binding protein reacting or binding specifically to said first ligand or first binding protein.

Then, advantageously, said first or second ligand or binding protein can react or be bound to a third binding protein bearing a said detectable substance such as a fluorochrome or luminescent substance or an enzyme such as peroxidase, said third binding protein binding specifically to a said first and/or second ligand or binding protein. Detecting said detectable substance via a said second ligand or second binding protein or third binding protein enables to amplify the signal of the said detectable substance.

More particularly, the first ligand or first binding protein can be:
biotin, said second and third binding protein being then avidin or streptavidin and, respectively, an antibody raised against biotin, or
avidin or streptavidin, said second ligand and said third binding protein being then biotin and, respectively, an antibody raised against avidin or streptavidin, or
a first antibody, said second and third binding protein being then a second and third antibody specific to said first antibody.

More particularly, said labeling molecule is a first ligand, preferably biotin, bearing a said second reactive group, and in step c) said living bacteria coupled to said first ligand are detected by reaction of said bacteria with an antibody specific to said first ligand, said antibody bearing a detectable substance, preferably a fluorochrome or luminescent molecule or an enzyme.

More particularly again, said labeling molecule is a first ligand, preferably biotin, bearing a said second reactive group, and in step c) said living bacteria coupled to said first binding protein is immobilized by reacting said first ligand with a solid substrate, preferably magnetic beads, coupled to a said second binding protein, preferably avidin or streptavidin, before detecting said living bacteria by bacterial DNA enzymatic amplification or by reaction of said bacteria with a third binding protein reacting or binding specifically to said first ligand or second binding protein, said third binding protein bearing a detectable substance, preferably a fluorochrome or luminescent molecule or an enzyme, said third binding protein being preferably an antibody specific to said first ligand or first binding protein.

Such embodiment wherein said living bacteria are immobilized on said solid substrate enables to concentrate the sample into said bacteria and to quantify said living bacteria by any known method including DNA enzymatic amplification such as PCR, especially Real Time PCR or a method involving immunological reaction with a labeled antibody such as an ELISA test.

More particularly, the present invention provides a method for specifically detecting living bacteria of a given category of bacteria in a sample comprising bacteria, said labeling molecule being a detectable molecule comprising a detectable substance, the method comprising the step c) of detecting living bacteria in detecting whether said bacteria comprise said detectable molecule bound to the glycans of their outer membrane.

Step a) results in labeling specifically all living bacteria of said category by incorporating into the glycans, especially lipopolysaccharide layer of the outer membrane of the living bacteria, a residue of said analog of monosaccharide compound.

Step b) results in bonding the said labeling molecule to the analog residue incorporated to the said glycans of living bacteria, especially LPS, by reacting the said first reactive group of the said modified monosaccharide within the said glycans, especially LPS of said cultivated bacteria, with a said labeling molecule comprising a said second reactive group under appropriate conditions and in the presence of appropriate suitable reactants.

In step a), preferably the said given position of the said endogenous monosaccharides is a position which comprises a free group in the said endogenous monosaccharide residue incorporated within said glycans of the outer membrane of the bacteria. By "free group" is meant a position not engaged in a covalent bond within the said glycans, especially LPS.

The modified ulosonic acid or ulosonate salt being metabolically assimilated led to the use of this method for fast detection—the overall process taking less than one day—of metabolically active/viable Gram negative bacteria. This method is very powerful in regard to the fact that detection of viable bacteria needs normally between 2 days and more than one month depending on the bacterial strain.

Severe pathogens are hiding amongst Gram negative bacteria, and the rapid identification of viable cells represents a major sanitary challenge. The present invention therefore provides a simple strategy to label the cell surface of metabolically active Gram negative bacteria, via metabolic incorporation of a modified ulosonic acid or ulosonate residue into their lipopolysaccharide, followed by further conjugation using click-chemistry.

The assimilation of an exogenous ulosonate analog, such as a KDO analog, in the bacterial cell, and its incorporation into the LPS in competition with its endogenous counterpart, such as KDO, was not obvious at all, since these molecules are highly polar and do not cross membranes easily. Attempts at using KDO analogs as antibacterials have failed due to the difficulty to reach a sufficient intracellular concentration of these analogs [10].

More particularly, the incubation time at step a) is from 1 hr to 24 hr, preferably from 2 hr to 12 hr and the monosaccharide analogue compound concentration is from $10^{-8}$M to 1M, more particularly $10^{-5}$M to 1M, for detecting a bacteria concentration of no more than $10^{11}$ cell/ml, more particularly no more than $10^9$ cell/ml.

Particularly, the said analog monosaccharide is a substituted ulosonic acid having one of the following formula (I) or (II) or an ulosonate salt thereof:

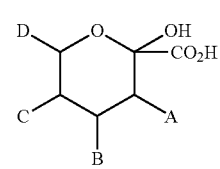

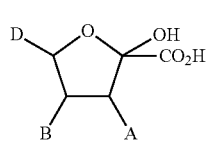

Wherein

A, B and C can be independently H, OH, NH$_2$, OH and NH$_2$ being substituted or not by protecting groups thereof, preferably OH and NH$_2$ being substituted by alkyl, hydroxyalkyl, acyl, formyl or imidoyl groups, and D is an alkyl chain in C$_2$ to C$_4$, each carbon being substituted or not by OH or NH$_2$, OH and NH2 being substituted or not by protecting groups thereof, preferably OH and NH$_2$ being substituted by alkyl, hydroxyalkyl, acyl, formyl or imidoyl groups, and at least one of A, B, C or D groups is substituted by a said first reactive group.

These two formula one with a pyranosic cycle (I) and the other with a furanosic cycle (II) correspond in fact to the two species naturally in equilibrium although generally the formula (I) is predominant.

More particularly, for OH the protecting group can be preferably an alkyl, hydroxyalkyl, acyl or formyl group.

More particularly, for NH2 the protecting groups can be selected among alkyl, hydroxyalkyl, acyl, formyl or imidoyl groups.

NH2 can be protected by one or two protecting groups, especially one CH3 group and one alkyl, hydroxyalkyl, acyl, formyl or imidoyl group, especially acetyl (Ac), acetimidoyl (Am), N-methyl-acetimidoyl, N,N-dimethyl-acetimidoyl, formyl (Fo), or hydroxybutanoyl group.

More particularly, the said analog of monosaccharide compound is a substituted octulosonic acid or octulosonate salt compound.

An octulosonic or octulosonate compound of formula (I) comprises as D group an alkyl chain in C$_2$.

An octulosonic acid or octulosonate compound of formula (II) comprises as D group an alkyl chain in C$_3$.

The said analog of monosaccharide compound can also be a substituted nonulosonic or nonulosonate salt compound.

A nonulosonic or nonulosonate compound of formula (I) comprises as D group an alkyl chain in C$_3$.

A nonulosonic or nonulosonate compound of formula (II) comprises as D group an alkyl chain in C$_4$.

Among the endogenous ulosonic acid or ulosonate residues, particularly frequent are the following ones which are specifically present in the following categories of bacteria:

1—Octulosonic acid or octulosonate residues of the following formula (I) wherein D is —CHOH—CH$_2$OH (Ia-1, Ia-2) or —CHOH—CH$_2$NH$_2$ (Ia-3):

1.1)

•(Ia-1)

(3-deoxy-D-manno-oct-2-ulosonic acid, or ketodeoxyoctonic acid), specific to the following category of bacteria: all Gram negative bacteria. It can be found in the LPS inner core of all Gram negative bacteria except some *Shewenella* bacteria, as well as the LPS O-antigen of *Providencia, Cronobacter* and *Pseudoalteromonas* bacteria and also found in some capsular polysaccharides (CPS) in *E. coli, Neisseria meningitidis, rhizobia, Actinobacillus pleuropneumoniae, Moraxella nonliquefaciens, Burkholderia pseudomallei, Burkholderia cepacia, Burkholderia caribensis, Pseudoalteromonas nigrifaciens*).

1.2)

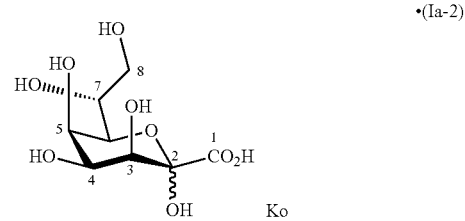

(D-glycero-D-talo-oct-2-ulosonic acid, or ketooctonic acid), (Ia-2) can be found in to the following category of bacteria: *Yersinia, Acinetobacter, Burkholderias*.

1.3)

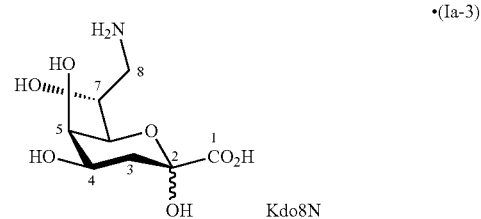

(8-amino-3,8-dideoxy-D-manno oct-2-ulosonic acid, (Ia-3) can be found in the *Schewanella* bacteria:

2—Nonulosonic acid or nonulosonate residues of the following formula wherein D is —CHNH$_2$—CHOH—CH$_3$ (Ib-1, Ib-2, Ib-5, Ib-6), —CHOH—CHOH—CH$_2$OH (Ib-3, Ib-4), —CHNH$_2$—CHNH$_2$—CH$_3$ (Ib-7):

2.1)

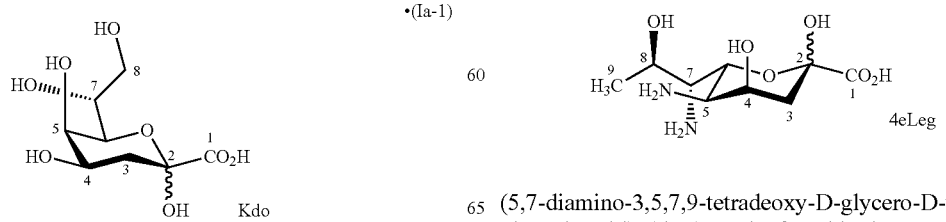

(5,7-diamino-3,5,7,9-tetradeoxy-D-glycero-D-talo-non-2-ulosonic acid), (Ib-1) can be found in the LPS of *Legionella pneumophila* bacteria and in *Schewanella japonica*.

2.2)

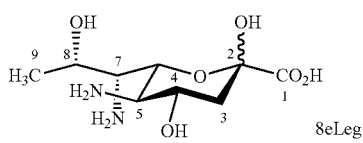

(5,7-diamino-3,5,7,9-tetradeoxy-L-glycero-D-galacto-non-2-ulosonic acid), (Ib-2) can be found in *E. coli* strains, *Providencia stuartii, Pseudomonas aeruginosa, Yersinia ruckeri, Salmonella arizonae, Morganella morganii, Shewanella putrefaciens*.

2.3)

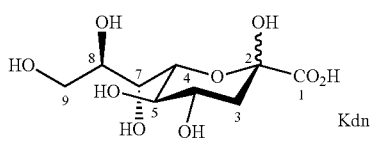

(3-Deoxy-D-glycero-D-galacto-non-2-ulosonic acid), (Ib-3) can be found in the CPS of *Klebsiella ozaenae* and *Sinorhizobium fredii* (in the form of 5-O-methyl Kdn). Kdn-containing polysaccharides or oligosaccharides have been found in the cell wall of Gram positive bacteria (order of Actinomycetales).

2.4)

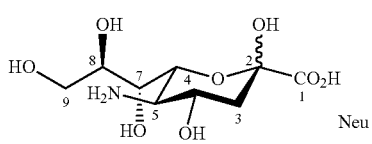

(5-amino-3,5-dideoxy-D-glycero-D-galacto-non-2-ulosonic acid), (Ib-4) can be found in the CPS of *E. coli, Neisseria meningitidis, Moraxella nonliquefaciens*, and *Mannheimia (Pasteurella) haemolytica, Streptococcus agalactiae* (Gram+), *Streptococcus suis* (Gram +) and in the LPS O-antigen of bacteria including *Hafnia alvei, Escherichia albertii, Salmonella enterica, E. coli, Citro-bacter, Vibrio cholerae, Shewanella* algae, and in the LPS core of several pathogens including *N. meningitidis, Neisseria gonorrhoeae, H. influenzae, Haemophilus ducreyi, Histophilus somni, Campylobacter jejuni*, and *Helicobacter pylori*.

2.5)

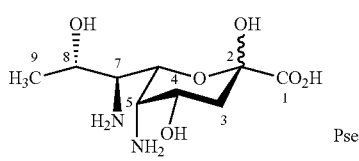

(5,7-diamino-3,5,7,9-tetradeoxy-L-glycero-L-manno-non-2-ulosonic acid) (Ib-5) can be found in the O-antigen (LPS) of *Pseudomonas aeruginosa, Shigella boydii, Escherichia coli, Proteus vulgaris, Pseudoalteromonas atlantica, Pseudoalteromonas distincta, Sinorhizobium fredii*, and *Vibrio cholerae, Pseudoalteromonas atlantica* and Cell wall of *Kribella* spp. 5 (Gram +) and *Actinoplanes utahensis* (Gram +) and LPS core of *Vibrio parahaemolyticus* and in flagellar glycoproteins of Gram positive *Campylobacter jejuni, Campylobacter coli, Helicobacter pylori*, and *Clostridium botulinum*, and in the CPS of *Sinorhizobium* bacteria.

2.6)

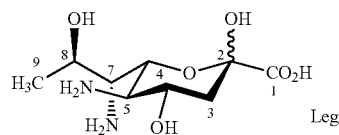

(5,7-diamino-3,5,7,9-tetradeoxy-D-glycero-D-galacto-non-2-ulosonic acid), (Ib-6). can be found in *Legionella pneumophila, Vibrio alginolyticus, Acinetobacter baumannii, Pseudomonas fluorescens*, and *Vibrio salmonicida*.

2.7)

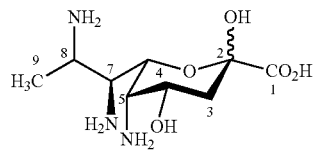

(Ib-7):5,7,8-triamino-3,5,7,8,9-pentadeoxynon-2-ulosonic acid (unknown configuration at C-8) can be found in *Tenacibaculum maritimum* (former *Flexibacter maritimus*).

In the above formula Ib-i, with i=1 to 7, $NH_2$ groups can be in the form of N-acetyl (NHAc), or can be in the form of N-acetimidoyl (NHAm), N—(N-methylacetimidoyl), N—(N,N-dimethylacetimidoyl), N-formyl (NHFo), NH-hydroxybutanoyl (NH-Hb), and can be further N-methylated or not.

Preferably, the said given category of bacteria comprises Gram negative bacteria and said endogenous monosaccharide residue of said LPS layer of the outer membrane of the bacteria is a deoxyoctulosonate residue and said analog of monosaccharide compound is a substituted deoxyoctulosonic acid or deoxyoctulosonate compound (also named ketodeoxyoctonate, so-called KDO).

By "Gram negative bacteria", it is meant that the method with the said KDO does not allow labeling of Gram positive bacteria and other Gram negative bacteria not bearing the same endogenous monosaccharide. Indeed, all of the Gram negative bacteria LPS comprise a said deoxyoctulosonate residues while it is not comprised in the glycans of Gram positive bacteria.

By "deoxyoctulosonate" also referred to as Kdo is meant a 3-deoxy-D-manno octulosonic acid salt residue of formula (Ia-1).

More particularly, the said deoxyoctulosonate residue is substituted by a said reactive group at a position selected among the positions 3, 4, 5, 7 or 8 of the monosaccharide cycle, preferably 3, 7 or 8. The position 2 of this endogenous monosaccharide is engaged in a covalent bond with the LPS.

All of the Gram negative bacteria comprise a said deoxyoctulosonate residue comprising free groups which can be substituted by a said first reactive group at one of these positions 3, 4, 5, 7 or 8 of at least one residue and all of the Gram negative bacteria comprise a free group at the position 8 of at least one residue except some *Shewenella* bacteria.

To detect specifically the Gram negative bacteria, it can be more advantageous to use a culture medium specific to Gram negative bacteria in steps a) and b) therefore not allowing culture of Gram positive bacteria.

More particularly, the said deoxyoctulosonate residue is a compound of formula (I) or (II), more particularly of formula (Ia-1), substituted by a said reactive group $R_1$ at the position 8 wherein D=—CHOH—$CH_2$—$R_1$, A=H, B=OH, C=OH in formula (I) or D=—CHOH—CHOH—$CH_2$—$R_1$, A=H, B=OH in formula (II).

More particularly, the said Gram negative bacteria having an endogenous incorporated KDO are selected among *E. coli, Salmonella typhimurium, Legionella pneumophila* and *Pseudomonas aeruginosa*. These bacteria present endogenous KDO free at the position 8.

Other Gram negative pathogens bacteria having at least one the positions of an ulosonic acid or ulosonate residue free can be selected among *Bacteroides fragilis, Bartonella bacilliformis, Bartonella quintana (Rochalimaea quintana), Bartonella* spp. *(Rochalimaea* spp.*), Bordetella bronchiseptica, Bordetella parapertussis, Bordetella pertussis, Brachyspira* spp, *Campylobacter fetus, Campylobacter jejuni, Campylobacter* spp, *Cardiobacterium hominis, Chlamydophila abortus, Chlamydophila caviae, Chlamydophila felis, Chlamydophila pneumoniae (Chlamydia pneumoniae), Edwardsiella tarda, Ehrlichia* spp, *Eikenella corrodens, Elizabethkingia meningoseptica (Flavobacterium meningosepticum, Chryseobacterium, eningosepticum), Enterobacter aerogenes (=Klebsiella mobilis), Enterobacter cloacae, Enterobacter* spp, *Enterococcus* spp, *Francisella tularensis* subsp. *holarctica* ("*Francisella tularensis* var. *palaearctica*"), *Francisella tularensis* type B), *Fusobacterium necrophorum, Haemophilus ducreyi, Haemophilus influenzae, Haemophilus* spp, *Helicobacter pylori, Campylobacter pylori, Klebsiella oxytoca, Klebsiella pneumoniae, Klebsiella* spp, *Legionella bozemanae* corrig. (*Fluoribacter bozemanae*), *Legionella pneumophila, Legionella* spp, *Leptospira interrogans, Leptospira interrogans sensu lato* inclut *Leptospira alexanderi, Leptospira borgpetersenii, Leptospira fainei, Leptospira inadai, Leptospira interrogans, Leptospira kirschneri, Leptospira noguchii, Leptospira santarosai, Leptospira weilii, Morganella morganii (Proteus morganii), Neisseria gonorrhoeae, Neisseria meningitidis, Neorickettsia sennetsu (Ehrlichia sennetsu, Rickettsia sennetsu), Pasteurella multocida, Pasteurella* spp, *Plesiomonas shigelloides, Porphyromonas* spp, *Prevotella* spp, *Proteus mirabilis, Proteus penneri, Proteus vulgaris, Providencia alcalifaciens, Providencia rettgeri (Proteus rettgeri), Providencia* spp, *Pseudomonas aeruginosa, Rickettsia* spp, excluding *Orientia (Rickettsia) tsutsugamushi, Rickettsia akari, Rickettsia canadensis, Rickettsia conorii, Rickettsia montanensis, Rickettsia prowazekii, Rickettsia rickettsia* et *Rickettsia typhi, Salmonella enterica* subsp. *Arizonae (Salmonella arizonae, Salmonella choleraesuis* subsp. *arizonae), Salmonella enterica* subsp. *enterica* sérovar Enteritidis *(Salmonella enteritidis), Salmonella enterica* subsp. *enterica* sérovar Paratyphi A *(Salmonella paratyphi)*, Paratyphi B, and Paratyphi C, *Salmonella enterica* subsp. *enterica* sérovar Typhimurium *(Salmonella typhimurium), Shigella boydii, Shigella dysenteriae*, except type 1, *Shigella flexneri, Shigella sonnei, Streptobacillus moniliformis*, "*Treponema carateum, Treponema pallidum,* "*Treponema pertenue*" ("*Treponema pallidum* subsp. *pertenue*"), *Treponema* spp, *Vibrio cholerae, vibrio parahaemolyticus (=Beneckea parahaemolytica), Vibrio* spp, *Yersinia enterocolitica, Yersinia pseudotuberculosis, Brucella melitensis* (sensu stricto), *Brucella melitensis* biovar Abortus *(Brucella abortus), Brucella melitensis* biovar Canis *(Brucella canis), Brucella melitensis* biovar Suis *(Brucella suis), Burkholderia mallei (Pseudomonas mallei), Burkholderia pseudomallei (Pseudomonas pseudomallei), Chlamydophila psittaci (Chlamydia psittaci), Coxiella burnetii, Francisella tularensis* subsp. *Tularensis* ("*Francisella tularensis* subsp. *nearctica*", *Francisella tularensis* biovar *Tularensis, Francisella tularensis* type A), *Orientia tsutsugamushi (Rickettsia tsutsugamushi), Rickettsia akari, Rickettsia canadensis* corrig, *Rickettsia conorii, Rickettsia montanensis* corrig, *Rickettsia prowazekii, Rickettsia rickettsii, Rickettsia typhi, Salmonella enterica* subsp. *enterica* sérovar Typhi *(Salmonella typhi), Shigella dysenteriae* type 1, *Yersinia pestis*.

In another preferred embodiment, the method according to the invention is for labeling, preferably detecting, specifically living *Legionella pneumophila* bacteria and the said given category of bacteria is the category of the *Legionella pneumophila* bacteria and said endogenous monosaccharide residue of said LPS layer of the outer membrane of the bacteria is a 4-epilegionaminic acid (5,7-diamino-3,5,7,9-tetradeoxy-D-glycero-D-talo-non-2-ulosonic acid) or 4-epilegionaminate residue, or a legionaminic acid (5,7-diamino-3,5,7,9-tetradeoxy-D-glycero-D-galacto-non-2-ulosonic acid) or legionaminate residue, and the said analog of a monosaccharide compound is respectively a substituted 4-epilegionaminic acid or 4-epilegionaminate compound, or a substituted legionaminic acid or legionaminate compound, preferably substituted at one position selected among the positions 3, 4, 5, 7, 8 and 9 of the monosaccharide cycle, preferably 5, 7 and 9. The position 2 of this endogenous monosaccharide is engaged in a covalent bond with the LPS.

Preferably, the said analog of a monosaccharide compound is a substituted 4-epilegionaminic acid or 4-epilegionaminate compound of formula (I), more particularly (Ib-1), or a substituted legionaminic acid or legionaminate compound of formula (I), more particularly (Ib-6), substituted by a said reactive group $R_1$ at the position 9 wherein D=—$CHNH_2$—CHOH—$CH_2R_1$, A=H, B=OH and C=$NH_2$.

Another preferred structure of the said analog of a monosaccharide compound is a substituted 4-epilegionaminic acid or 4-epilegionaminate compound of formula (I), more particularly (Ib-1), or a substituted legionaminic acid or legionaminate compound of formula (I), more particularly (Ib-6), substituted by a said reactive group $R_1$ at, at least, one of the positions 5 and 7, wherein D=—$CHNHR_2$—CHOH—$CH_3$, A=H, B=OH and C=$NHR_3$, with $R_2$ and $R_3$ being independently one of each other either H or $R_1$.

In another preferred embodiment, the method according to the invention is for labeling, preferably detecting, specifically living *Pseudomonas aeruginosa* bacteria and the said given category of bacteria is the category of the *Pseudomonas aeruginosa* bacteria and said endogenous monosaccharide residue of said LPS layer of the outer membrane of the bacteria is a 8-epilegionaminic acid (5,7-diamino-3,5,7,9-tetradeoxy-L-glycero-D-galacto-non-2-ulosonic acid) or 8-epilegionaminate residue, or a pseudaminic acid (5,7-diamino-3,5,7,9-tetradeoxy-L-glycero-L-manno-non-2-ulosonic acid) or pseudaminate residue, and the said analog of a monosaccharide compound is respectively a substituted 8-epilegionaminic acid or 8-epilegionaminate compound, or a substituted pseudaminic acid or pseudaminate compound, preferably substituted at one position selected among the positions 3, 4, 5, 7, 8 and 9 of the monosaccharide cycle, preferably 5, 7 and 9. The position 2 of this endogenous monosaccharide is engaged in a covalent bond with the LPS.

Preferably, the said analog of a monosaccharide compound is a substituted 8-epilegionaminic acid or 8-epilegionaminate compound of formula (I), more particularly (Ib-2), or a substituted pseudaminic acid or pseudaminate compound of formula (I), more particularly (Ib-5), substituted by a said reactive group $R_1$ at the position 9 wherein D=-$CHNH_2$—CHOH—$CH_2R_1$, A=H, B=OH and C=$NH_2$.

Another preferred structure of the said analog of a monosaccharide compound is a substituted 8-epilegionaminic acid or 8-epilegionaminate compound of formula (I), more particularly (Ib-2), or a substituted pseudaminic acid or pseudaminate compound of formula (I), more particularly (Ib-5), substituted by a said reactive group $R_1$ at, at least, one of the positions 5 and 7, wherein D=—CHN$HR_2$—CHOH—$CH_3$, A=H, B=OH and C=$NHR_3$, with $R_2$ and $R_3$ being independently one of each other either H or $R_1$.

More particularly, the said detectable substance is a fluorochrome or luminescent molecule detectable by fluorescence or luminescence.

Preferably, the said first reactive group $R_1$ is selected among groups consisting in or bearing the group azido (—$N_3$) and groups consisting in or bearing the group alkyne (—C≡C—), and the said second reactive group $R_2$ is selected among groups consisting in or bearing respectively the groups alkyne (—C≡C—) and azido (—$N_3$), and reacting the said azido reactive group with a said alkyne group (—C≡CH), is carried out in performing an azide alkyne cycloaddition.

An azide alkyne cycloaddition is a well-known so-called click chemistry reaction in the presence of a Copper catalyst wherein the azide group reacts with the alkyne group to afford a triazole.

More particularly, the reaction is carried out in copper catalyzed conditions in the presence of a tris-triazolyl ligand, preferably TGTA.

More particularly, the detectable molecule is a fluorophore bearing a terminal alkyne group.

More particularly, the Kdo analog replacing endogenous 3 deoxy-D-manno octulosonic acid incorporated into the LPS layer of the outer membrane of the bacteria, is a Kdo-$N_3$ (8-azido-3,8-dideoxy-D-manno-octulosonic acid) analog reacting in the presence of a tris-triazole ligand such as TGTA (Tris((1-(β-D-glucopyranosyl)-1H-[1,2,3]-triazol-4-yl)methyl)amine) or TBTA (Tris-[(1-benzyl-1H-1,2,3-triazol-4-yl)methyl]amine) and an Alexa labeling fluorophore molecule bearing a terminal alkyne group with a catalyst so as to perform an azide alkyne cycloaddition of the said fluorophore and said Kdo-$N_3$.

Other appropriate ligands frequently used are: tris(3-hydroxypropyltriazolylmethyl)amine (THPTA), 2-(4-((bis((1-tert-butyl-1H-1,2,3-triazol-4-yl)methyl)amino)methyl)-1H-1,2,3-triazol-1-yl)ethanesulfonic acid (BTTES), Tris((1-((O-ethyl) carboxymethyl)-(1,2,3-triazol-4-yl)) methyl) amine, Bathophenanthroline disulfonate, or Tris(2-benzimidazolylmethyl)amines (53).

Other reactive groups and other reactions are possible such as: Staudinger Ligation (first reactive group=azide and second reactive group=phosphine), copper-free click-chemistry (first reactive group=azide and second reactive group=constrained alkyne (intracyclic alkyne)), carbonyl condensation (first reactive group=aldehyde or ketone and second reactive group=hydrazide or oxyamine), His-tag (first reactive group=oligo-histidine and second reactive group=nickel-complex or nickel ligand), thiol-ene click chemistry (first reactive group=thiol and second reactive group=alkene), nitrile-oxide-ene click chemistry (first reactive group=nitrile oxide or aldehyde, oxime, or hydroxymoyl chloride or chloroxime and second reactive group=alkene or alkyne), nitrile imine-ene click chemistry (first reactive group=nitrile imine or aldehyde, hydrazone, or hydrazonoyl chloride or chlorohydrazone and second reactive group=alkene or alkyne), inverse electron demand Diels-Alder ligation (first reactive group=alkene and second reactive group=tetrazine), Suzuki-Miyaura coupling (first reactive group=aryl halide and second reactive group=aryl boronate).

In the above-mentioned listing of groups involved in the reactions, the first reactive group and the second reactive group can be permuted.

Other and higher specificity of detection can be obtained in incubating the bacteria sample with two said different monosaccharide analog compounds and two different detectable molecules.

In another particular embodiment of the method of the present invention, the said incubation of step a) and reaction of step b) are carried out on a membrane filter so that the cultivated bacteria emanating from a same original bacterium which has been multiplied are grouped together and can be visualized with a microscope and the said detectable molecule can be detected by visualization with a said microscope. Therefore, the number of cultivable bacteria can be quantified thereby.

This embodiment enables to filter the tested sample on said membrane filter such as a polyester membrane, prior to assimilation of the said modified monosaccharide to avoid over-estimation of viable bacteria due to possible growth during the assimilation period. Indeed, when cells fixed on the top of such membrane start to grow, they stay together and form a micro colony that can be easily detected as coming from the same single cell. Therefore, this enables to number by counting the cultivable bacteria.

The present invention also provides a kit for carrying out the method of the invention comprising:
  a said analog of a monosaccharide compound comprising an ulosonic acid or ulosonate compound substituted at a given position by a said first reactive chemical group, and
  a said labeling molecule comprising a said second reactive group capable of reacting with said first reactive group, and
  reactants for generating the reaction of said first reactive group of said analog residue incorporated within said glycans of the outer membrane of said bacteria with said second reactive group of said labeling molecule, and
  a culture or incubation medium allowing the growth of a said given category of bacteria, preferably specific to the growth of said given category of bacteria, and Preferably, the said culture or incubation medium further comprises agents enhancing and/or accelerating the growth speed and/or the capacity to form colonies of the said given category of bacteria. More particularly, the incubation medium comprises at least an antioxidant agent such as pyruvate or catalase.

More particularly, in one embodiment, the kit further comprises:
- a said detectable molecule or said second molecule bearing a detectable substance, preferably a fluorochrome or luminescent molecule or an enzyme, and/or
- a solid substrate bearing a said second molecule capable of specifically reacting or binding with said labeling molecule.

More particularly, in one embodiment, the kit of the present invention further comprises:
- a said detectable molecule comprising a said second reactive group capable of reacting with said first reactive group, and
- a solid medium allowing visualization of the bacteria after incubating with the said analog of a monosaccharide compound, said reactants and said detectable molecule.

More particularly again, the kit comprises:
- a said analog of a monosaccharide compound being a deoxyoctulosonic acid or deoxyoctulosonate salt compound substituted by a said first reactive group comprising an azido or alkyne group, and
- a said second reactive group of the detectable molecule bearing an alkyne or, respectively, azido group, and
- said reactants comprising a copper catalyst and a tris-triazolyl ligand.

Other characteristics and advantages of the present invention will be more apparent in the light of the following detailed description referring to the following figures wherein:

FIG. 1A shows the Structure of the major component of E. coli K12 lipopolysaccharide, with the KDO sugar residue incorporated within IC, the Inner core of the LPS of Gram negative bacteria between OC, the outer core and LA, the lipid A, showing the anchoring site A for O-antigen and the possible site of modification B of KDO in position 8; Glc: D-glucose; GlcN: 2-amino-2-deoxy-D-glucose; KDO: 3-deoxy-D-manno-octulosonate; Hep: L-glycero-D-manno-heptose; Gal: D-galactose;

Figure 3A:
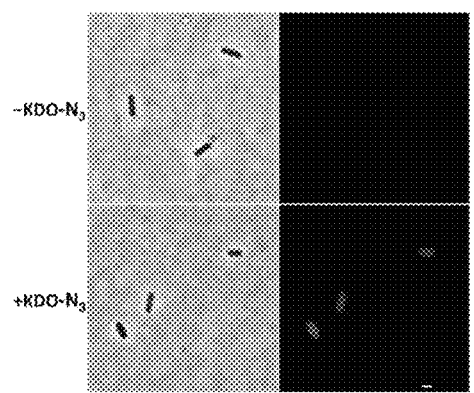
FIG. 3A represents photography of E. coli K12 with metabolically incorporated KDO-$N_3$ (+KDO-$N_3$) and without metabolically incorporated KDO (−KDO-$N_3$) before it is revealed via A488-yne—Cu(I) catalyzed click chemistry after 5 min. (in grey) and after it is revealed (in black)
Figure 3B:
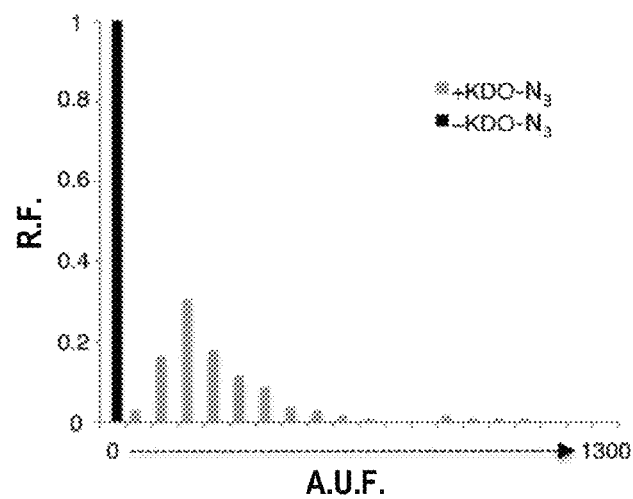
FIG. 3B represents a graphic of frequency distribution of the bacterial fluorescence values generated and plotted with (grey bars) or without (black bars) adding KDO-$N_3$, the arbitrary unit of fluorescence ("a.u.f.") range being from 0 to 1300 in abscissa and the relative frequency ("r.f.") range being from 0 to 1.
Figure 3C:
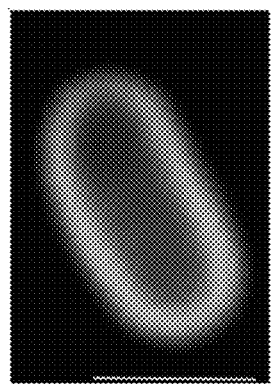
FIG. 3C is a photography showing fluorescence concentrated at the cellular surface of E. coli labelled via A488-yne—Cu (I) catalyzed click chemistry during 5 min, the image being deconvolved using Richardson-Lucy algorithm with an experimental point spread fusion.
Figure 4:
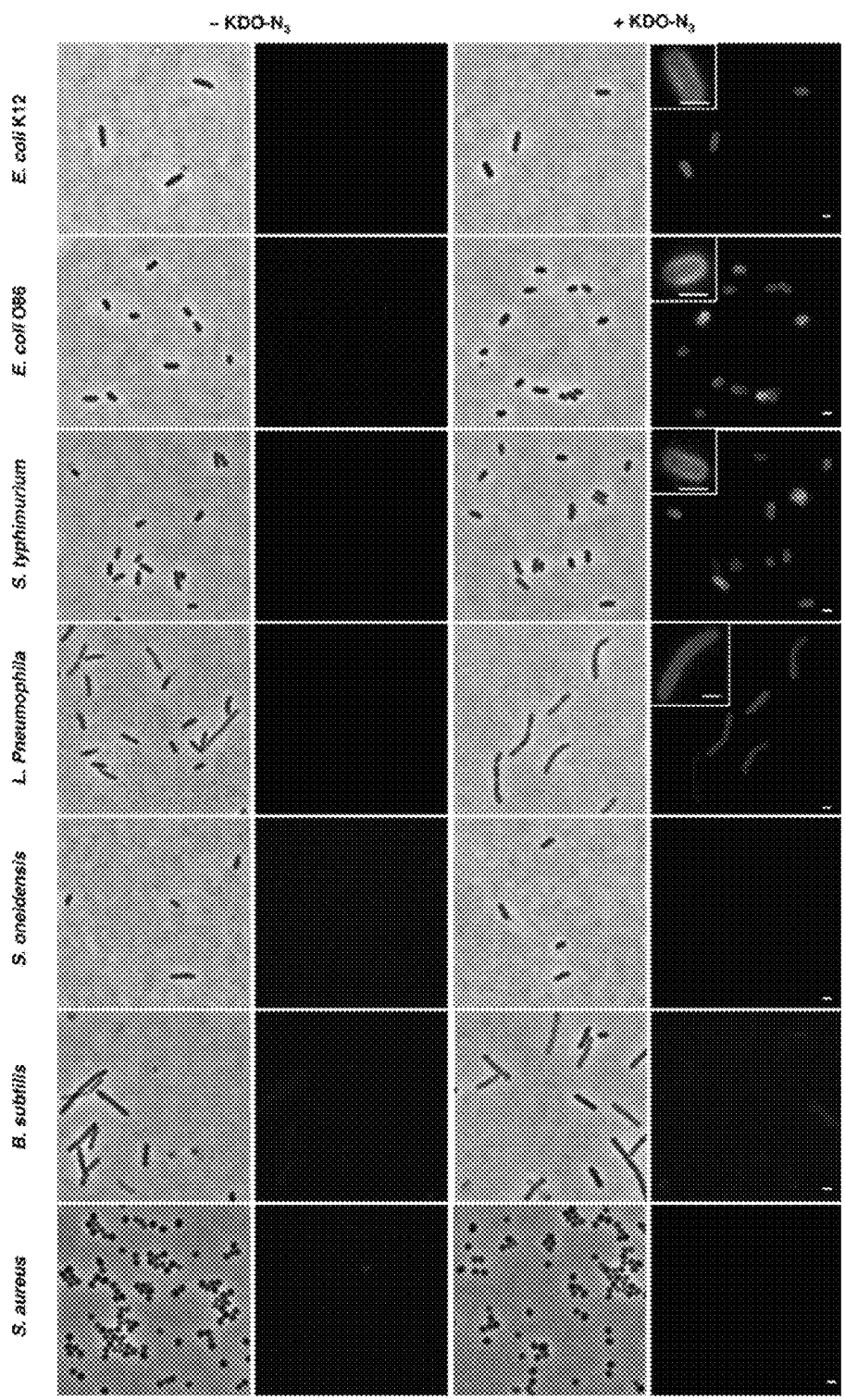
Figure 5:
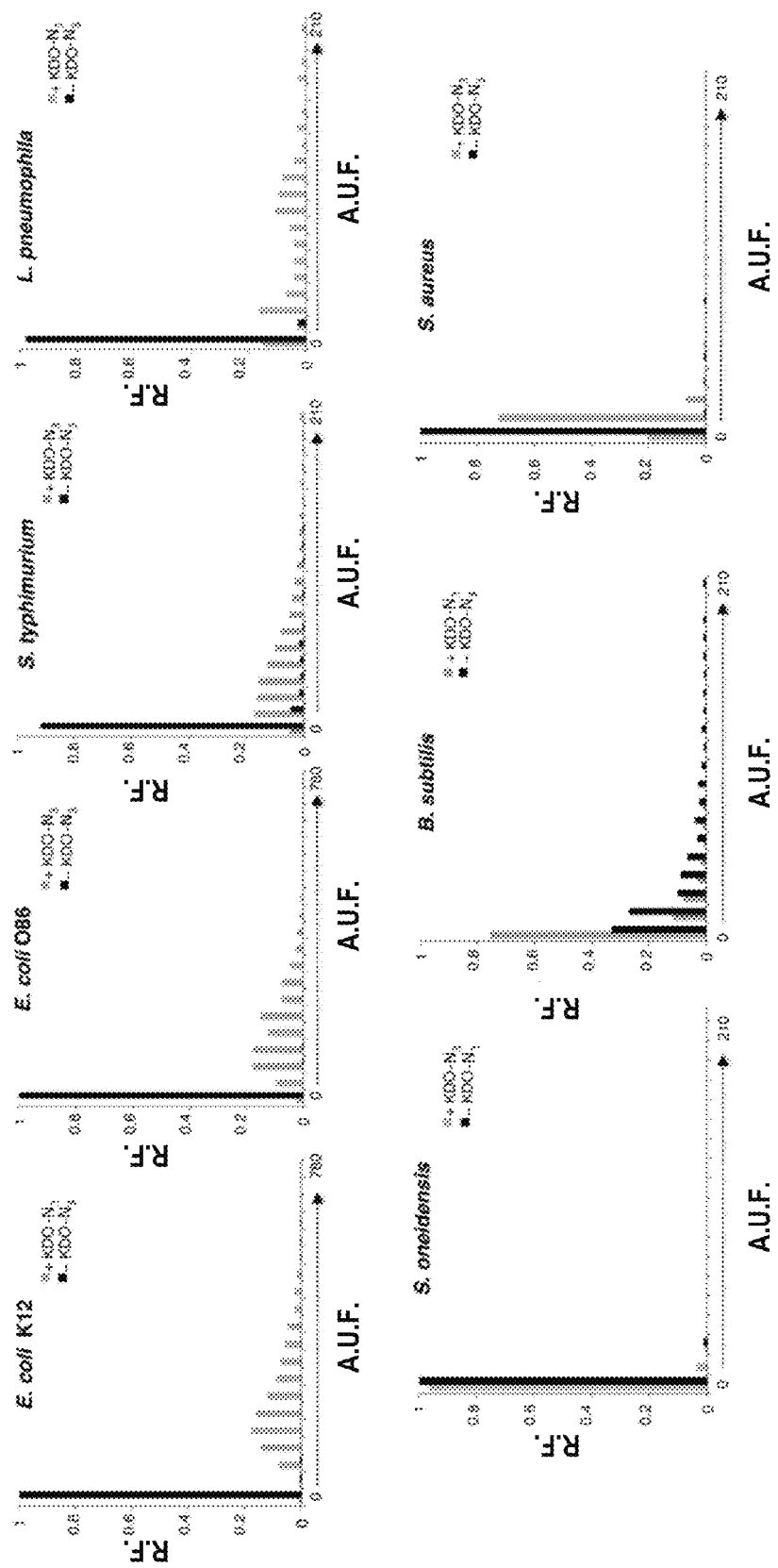

FIG. 4 are photographs representing the detection of metabolically incorporated KDO-$N_3$ by various bacterial strains, metabolically incorporated KDO-$N_3$ by various bacteria was revealed via A488-yne—Cu(I) catalyzed click chemistry after 60 min. Phase contrast and fluorescence images (Left panel) without adding KDO-$N_3$; (right panel) with adding KDO-$N_3$. Scale bar 1 μm as in FIG. 3 A (bacteria with added KDO-$N_3$ (+KDO-$N_3$) and without added KDO (−KDO-$N_3$) before it is revealed via A488-yne—Cu(I) catalyzed click chemistry after 5 min in grey and after it is revealed in black; and FIG. 5 represents the results (photographs and graphics) of detection of metabolically incorporated KDO-$N_3$ by various bacterial strains. Metabolically incorporated KDO-$N_3$ by various bacterial strains was revealed via A488-yne—Cu(I) catalyzed click chemistry after 60 min. Frequency distribution of the bacterial fluorescence values was generated and plotted with (grey bars) or without (black bars) adding KDO-$N_3$.

The following description is the description of an illustrative example of click labeling of bacterial membranes of Gram negative bacteria via metabolic modification of the LPS inner-core with modified KDO.

Figure 1A:
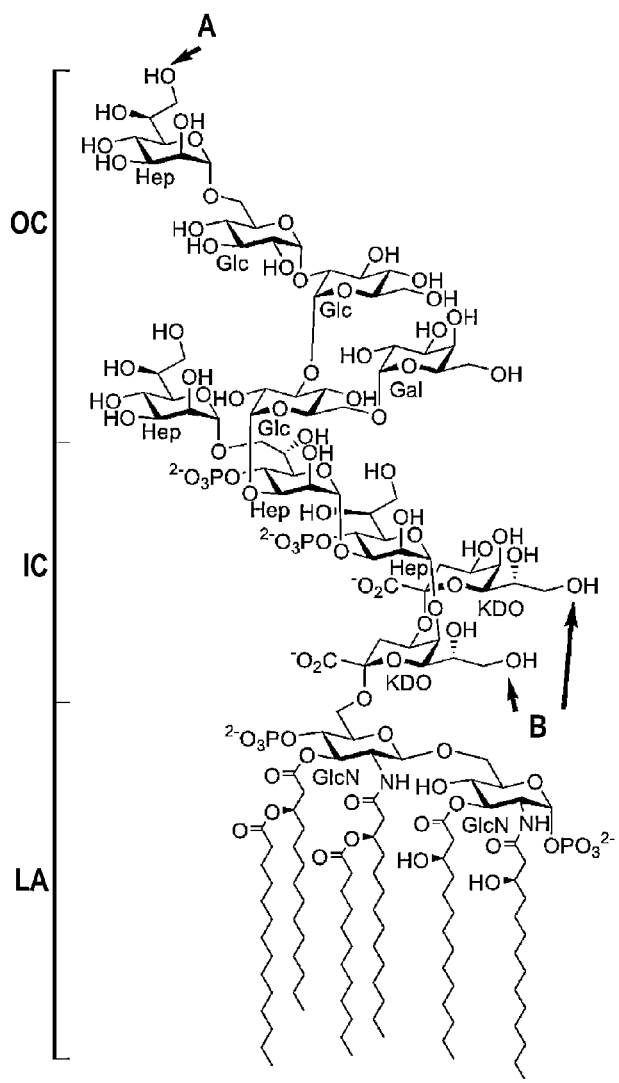
FIG. 1B shows the KDO biosynthetic pathway (KDO pathway)
Figure 1B:
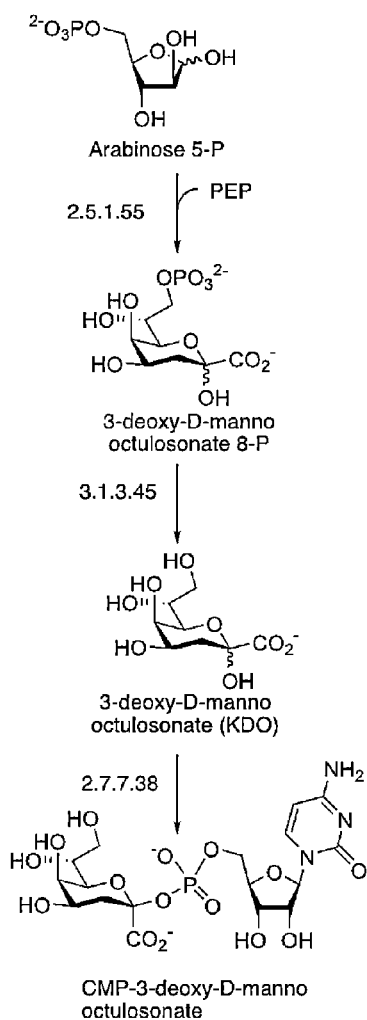

Viable Gram-negative bacteria can specifically incorporate a modified KDO into their Lipopolysaccharides, decorating the cell surface with a bio orthogonal chemical reporter. Click-chemistry allows further labeling of viable cells, in an overall rapid process as schematically shown in FIG. 1.

EXAMPLE 1

Assimilation of 8-azido-3,8-dideoxy-D-manno-octulosonic acid (KDO-$N_3$) and specific detection of Gram negative bacteria 1) Within all potential targets, 3-deoxy-D-manno-octulosonic acid (KDO) appears to be a very attractive candidate. Indeed, KDO is a specific and essential component of the inner core of LPS, [7,8] and has long been considered as being present in the LPS of almost all Gram negative species (as well as higher plants and algae), where at least one residue is directly connected to lipid A (FIG. 1A). [9] Due to its vital importance, KDO has been considered as a determinant for the characterization of Gram negative bacteria, and the KDO pathway as a potential target for the development of new antibacterials. [10] In this pathway (FIG. 1B), arabinose-5-P is condensed with PEP, leading to the formation of KDO-8-P, which is then transformed into free KDO, and further activated in the form of the CMP-KDO donor, prior to LPS elaboration.

Figure 2A:
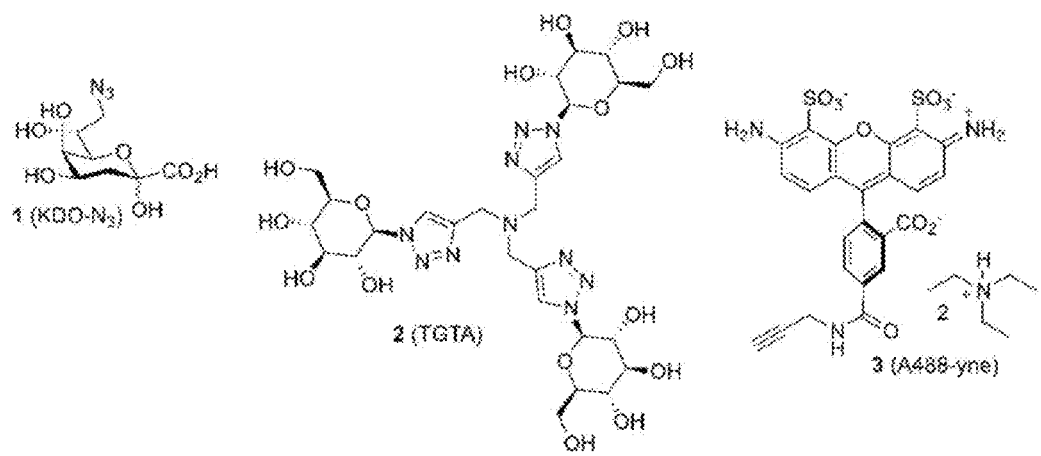
FIG. 2A shows the molecules used in this example (1=KDO-$N_3$, 2=TGTA, 3=A488-yne)
Figure 2B:
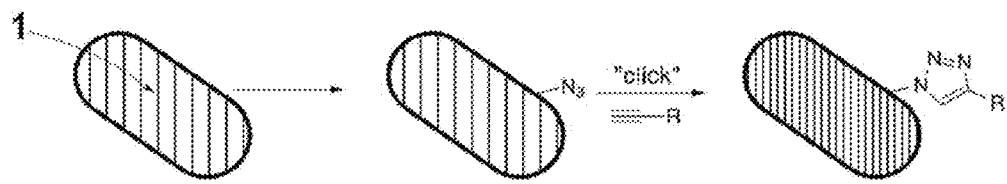
FIG. 2B shows a schematic representation of metabolic LPS labelling of E. coli with 1=KDO-$N_3$.

For all these reasons, it has been sought whether this KDO pathway, as a LPS-specific pathway, could be tolerant enough to incorporate a modified KDO, such as 8-azido-8-deoxy-KDO (1, FIG. 2A), into the core of E. coli LPS, and potentially other Gram negative bacteria. Given the presence of free KDO as an intermediate in the pathway, we postulated that if cell penetration of this analogue of KDO could be sufficient, [11] it could then potentially be directly activated, partially replace endogenous KDO into LPS, and be detected on the cell surface by azide-alkyne click chemistry (FIG. 2B). [12] Moreover, modification of the C-8 position of KDO by a bio orthogonal azido group should prevent reverse metabolism by KDO-8-P phosphatase (3.1.3.45), limiting the potential dissemination of the chemical reporter into other carbohydrates and metabolites.

Amongst the many potential multi-step synthetic strategies available to access 8-azido-3,8-dideoxy-D-manno-octulosonic acid 1, [13] this compound has been prepared in a straightforward manner (Scheme 1) [14] adapted from the approach described in 1963 by Ghalambor and Heath for direct KDO synthesis. [15] Namely 5-azido-5-deoxy-D-arabinofuranose [16] (6) was condensed with sodium oxaloacetate (7), leading after decarboxylation in slightly acidic conditions to KDO-N₃ (1), which was isolated as its ammonium salt in 57% yield (86% based on recovered 6). The 5-azido-5-deoxy-D-arabinofuranose precursor 6 could be obtained in a very direct, simple and time-saving strategy from commercial D-arabinose, as described herein after.

1a) Synthesis of ammonium 5-azido-5-deoxy-D-arabinofuranose 6.

The 5-azido-5-deoxy-D-arabinofuranose precursor 6 could be obtained in a very direct, simple and time-saving strategy, avoiding the alternative use of a bulky temporary trityl protection: commercial D-arabinose was directly tosylated on the primary position of its furanose forms, further acetylated, and subjected to nucleophilic displacement by azide anion without intermediate purification. At this step, the product could be easily separated from any other byproduct by flash chromatography. Final deacetylation afforded 6 in 15% overall yield.

Scheme 1. Synthesis of ammonium 5-azido-5-deoxy-D-arabinofuranose 6.

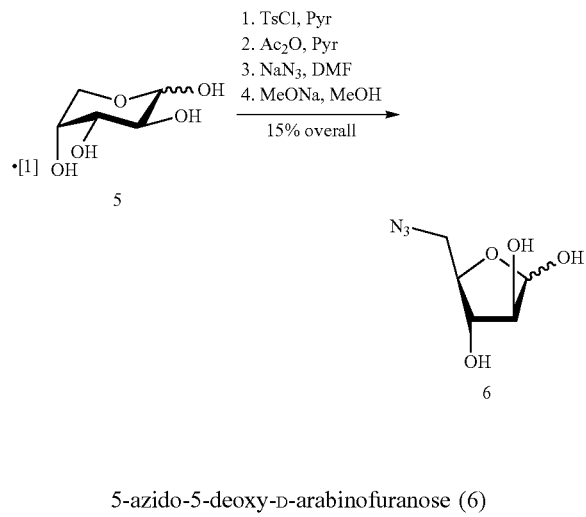

5-azido-5-deoxy-D-arabinofuranose (6)

Commercial D-Arabinose 5 (6.00 g, 40 mmol) was heated at 100° C. for 2 hours in pyridine (40 ml). The solution was allowed to cool down, further treated with tosyl chloride (8.38 g, 44 mmol; 1.1 equiv.), and stirred for 16 hours at room temperature. Acetic anhydride (20 ml) was then added. After complete acetylation, as determined by TLC, solvents were evaporated, and residual traces were co-evaporated several times with toluene. The residue was dissolved in DMF (100 ml), NaN₃ (5.20 g, 80 mmol, 2 equiv.) was added, and the suspension was heated at 80° C. for 20 hours. After dilution with ethyl acetate and washing with water, the organic layer was dried over anhydrous magnesium sulfate and concentrated. The residue was purified by flash chromatography (Petroleum ether/Ethyl acetate 7:3). The first eluted product was determined to be the expected 5-azido-1,2,3-tri-O-acetyl-D-arabinofuranose (1.83 g, 15%, α/β~2: 1). LRMS (ESI⁺) 324.0 [M+Na]⁺; HRMS (ESI⁺) calculated for [C₁₁H₁₅N₃NaO₇]+324.0802. found: 324.0802; ¹H NMR (CDCl₃, 360 MHz) δ (ppm): 6.41 (d, 0.33H, $J_{1,2}$ 3.5 Hz, H-1β); 6.23 (d, 0.67H, H-1α); 5.40-5.37 (m, 1.34H, H-2β, H-3β); 5.23 (d, 0.67H, $J_{1,2}$~1 Hz, H-2α); 5.06 (d, 0.67H, $J_{3,4}$ 4.6 Hz, H-3α); 4.30 (ddd, 0.67H, H-4α); 4.16-4.10 (m, 0.33H, H-4β); 3.69 (dd, 0.67H, $J_{4,5a}$ 3.1 Hz, $J_{5a,5b}$ 13.5 Hz, H-5aα); 3.61 (dd, 0.33H, $J_{4,5b}$ 3.6, $J_{5a,5b}$ 13.1 Hz, H-5aβ); 3.51-3.43 (m, 1H, H-5bα, H-5bβ); 2.15, 2.13, 2.12, 2.11, 2.11, 2.09 (6s, 18H, 6 CH₃CO); ¹³C NMR (CDCl₃, 62.5 MHz) δ (ppm): 170.3, 170.0, 169.1 (OC(O)CH₃), 99.2 (C-1α), 93.5 (C-1β), 84.1 (C-4α), 80.8 (C-4β), 80.6 (C-3α), 77.4 (C-2α), 75.1 (C-2β), 74.8 (C-3β), 53.0 (C-5β), 51.3 (C-5α), 20.9, 20.6, 20.3 (OC(O)CH₃).

1b) Protected 5-azido-1,2,3-tri-O-acetyl-D-arabinose was then dissolved into anhydrous methanol (30 ml), treated with a methanolic solution of MeONa (0.2 mol·l⁻¹, 3 ml) and stirred at room temperature for 3 h under an argon atmosphere. After neutralization (Dowex 50 (H⁺)) filtration, and concentration, 5-azido-5-deoxy-D-arabinofuranose 6 was obtained in 99% yield (1.03 g). LRMS (ESI⁺) 198.0 [M+Na]⁺, 40%, 230 [M+MeOH+Na]⁺, 100%; HRMS (ESI⁺) calculated for [C₅H₉N₃NaO₄]⁺198.0485. found: 198.0485; ¹H NMR (D₂O, 300 MHz) δ (ppm): 5.20 (d, 0.45H, $J_{1,2}$ 3 Hz, H-1β); 5.16 (d, 0.55H, $J_{1,2}$ 3 Hz, H-1α); 4.12-4.05 (m, 0.55H, H-4α); 4.02-3.85 (m, 2H, H-2α, H-2β, H-3α, H-3β); 3.84-3.76 (m 0.45H, H-4β); 3.56 (dd, 0.55H, $J_{5a,5b}$ 13.5, $J_{4,5a}$ 3.0 Hz, H-5aα); 3.51 (dd, 0.45H, $J_{5a,5b}$ 13.0 Hz, $J_{4,5a}$ 3.5 Hz, H-5aβ); 3.35 (dd, 0.55H, $J_{4,5b}$ 6.5 Hz, H-5bα); 3.33 (dd, 0.45H, $J_{4,5b}$ 6.5 Hz, H-5bβ); ¹³C NMR (D₂O, 75 MHz) δ (ppm): 101.1 C-1α; 95.3 C-1β; 81.4, 81.3, 79.7, 76.4, 75.9, and 74.8 C-2α,2β, 3α, 3β, 4α, 4β; 52.7 C-5β; 51.6, C-5α.

1c) Synthesis of Ammonium 8-azido-3,8-dideoxy-D-manno-octulosonate (1.NH₃).

A cool (4° C.) solution of 5-azido-5-deoxy-D-arabinofuranose 6 (437 mg, 2.5 mmol) in water (2.1 mL) was added to a solution of oxaloacetic acid (528 mg, 4.0 mmol) in water (2.5 mL), the pH of which has been adjusted to ~11 by addition of aqueous NaOH (10M). After being stirred for two hours at room temperature, the solution was neutralized (Dowex 50 (H⁺)), filtrated, and heated 20 min. at 80° C.

After its pH had been adjusted to ~7 with AcOH (0.5M), the mixture was purified by anion exchange chromatography (Dowex 1×8 (HCO₂⁻)). Initial elution with water gave unreacted 6 (150 mg, 34%). Further elution with a concentration gradient of formic acid (0.5 mol·l⁻¹→2 mol·l⁻¹), freeze-drying, treatment with a Dowex 50 (H⁺) resin, and neutralization by ammonia (0.2 mol·l⁻¹), gave after concentration, ammonium 8-azido-3,8-dideoxy-D-manno-octulosonate (1•NH₃, 400 mg, 57%).

Rf 0.38 (isopropyl alcohol/water 9:1). LRMS (ESI⁻) 262.1 [M-H]⁻, 100%; 525.1 [2M-H]⁻, 5%; 547.1 [2M−2H+Na]⁻, 10%; HRMS (ESI⁻) calculated for [C₈H₁₂N₃O₇]⁻ 262.0681. found: 262.0667. IR ν (cm⁻¹)=3210, 2111 (N₃), 1604, 1401, 1077. NMR of 1, like free KDO and derivatives, is complicated due to the presence of multiple forms (e.g. α-pyranose (αp, 58%), β-pyranose (βp, 4%), α-furanose (αf, 24%), β-furanose (βf, 14%)). Selected NMR data: ¹H NMR (D₂O, 400 MHz) δ (ppm): 3.56 (dd, $J_{8a,8b}$ 13.2, $J_{7,8a}$ 2.4 Hz, H-8aαp); 3.39 (dd, $J_{7,8b}$ 6.0 Hz, H-8bαp); 2.55 (dd, $J_{3a,3b}$ 14.3 Hz, $J_{3a,4}$ 7.2 Hz, H-3aαf); 2.33 (dd, $J_{3a,3b}$ 13.1, $J_{3a,4}$ 6.6 Hz, H-3aβf); 2.26 (dd, $J_{3b,4}$ 7.3 Hz, H-3bβf); 2.03 (dd, $J_{3b,4}$ 3.6, H-3bαf); 1.94 (dd, $J_{3a,3b}$=12.7, $J_{3a,4}$ 12.7 Hz, H-3aαp); 1.84 (dd, $J_{3b,4}$=4.9, H-3bαp); 1.71 (dd, $J_{3a,3b}$ $J_{3b,4}$ 12.0 Hz, H-3bβp); ¹³C NMR (D₂O, 100 MHz) δ (ppm): 176.4 (C-1αp), 104.1 (C-2αf), 96.2 (C-2αp), 85.3 (C-5αf), 71.5, 68.0, 66.3 and 66.0 (C-4-αp, 5αp, 6αp, 7αp), 53.8 (C-8αp), 44.6 (C-3αf), 33.5 (C-3αp).

Scheme 2. Synthesis of ammonium 8-azido-3,8-dideoxy-D-manno-octulosonate.

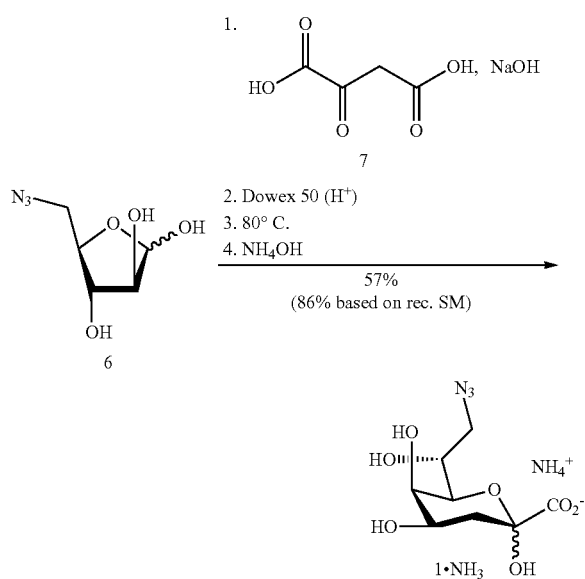

2) Non-pathogenic *E. coli* K12, which lacks an O-antigen, [17] was cultured overnight in the presence of KDO-N$_3$ (1) as described in the following paragraph 3), and further treated, during a time course experiment, using optimized copper-catalyzed click conditions [18] as described in the following paragraph 2a), in the presence of a glucose-derived tris-triazolyl ligand (2) [19] and an Alexa Fluor 488 fluorophore bearing a terminal alkyne group (3). After 5 min of incubation, a very bright labeling of bacteria was observed, while control experiments (in the absence of the KDO-N$_3$ analogue) did not show any signal (FIG. 3A, B). Fluorescence was carried out as described in the following paragraph 2b). Fluorescence was mostly evident around the cell periphery suggesting that membrane were preferentially labeled as expected (FIG. 3C).

2a) Copper Catalyzed Click Chemistry.

Overnight cultures were diluted 1000 times in fresh medium (final volume 100 μl) containing KDO-N$_3$ (4 mM). Bacteria were incubated at 37° C. for 12 hours and then washed 3 times with phosphate buffer (0.05 M, pH 7.5) by centrifugation at 13000×g for 1 min at room temperature.

CuSO$_4$ and TGTA, at a final concentration of 2 mM and 4 mM respectively, were mixed overnight in a phosphate buffer (0.05 M, pH 7.5) at 37° C. under vigorous shaking. Next, aminoguanidine, sodium ascorbate and A488-yne at final concentrations of 4 mM, 5 mM and 0.13 mM respectively were added to CuSO$_4$/TGTA overnight mix. Finally, bacteria were re-suspended in this solution. After 5, 30, 60 or 180 minutes, cells were washed 3 times with phosphate buffer by centrifugation at 13000×g for 1 min at room temperature and analyzed by microscopy.

2b) Fluorescence Microscopy.

Bacteria were inoculated onto glass cover slips and then covered with a thin (1 mm of thickness) semisolid 1% agar pad made with dilute LB (1/10 in phosphate buffer). Images were recorded with epifluorescence automated microscope (Nikon TE2000-E-PFS, Nikon, France) equipped with a CoolSNAP HQ 2 camera (Roper Scientific, Roper Scientific SARL, France) and a 100×/1.4 DLL objective. Excitation light was emitted by a 120 W metal halide light and signal was monitored using appropriate filters. Digital analysis and image processing were conducted by a custom automation script (Visual Basic) under Metamorph 7.5 (Molecular Devices, Molecular Devices France, France), as previously described [50,51].

3) To further consolidate this approach, its efficiency and specificity have been tested on three other Gram negative bacteria that use KDO (O86 *E. coli, Salmonella typhimurium, Legionella pneumophila* strain Paris) as well as three negative controls, including *Shewanella oneidensis*, which has recently been shown to use 8-amino-8-deoxy-KDO instead of KDO [21] and two Gram positive bacteria (*Bacillus subtilis, Staphylococcus aureus*) which do not produce KDO. [22]

The bacterial strains and growth conditions were as follows. *E. coli* K12, *E. coli* O86 and *S. typhimurium* 12023 were grown in M9 medium (containing also: casamino acid 0.2%, Glucose 0.2%, CaCl$_2$ 1 mM, MgSO$_4$ 5 mM), *S. oneidensis, B. subtilis* and *S. aureus* were grown in Luria-Bertani (LB) medium and *L. pneumophila* sp. Paris was grown in yeast extract medium supplemented with L-cysteine, ferric pyrophosphate and α-ketoglutarate (YEC). All strains were grown in a rotary shaker (160 rpm) at 37° C. except *S. oneidensis* which was grown at 28° C.

As expected, when the two *E. coli* strains, *S. typhimurium* and *L. pneumophila* Paris showed efficient and well defined cell-surface labeling, and no labeling was observed with *S. oneidensis* or Gram positive bacteria because these bacteria do not present KDO at their cell surface (FIG. 4 and FIG. 5).

4) Incubation and Reaction on Membrane Filter.

Samples containing bacteria were filtered through 25-mm, 0.45-mm-pore-size black polyester membrane filters. Individual membranes were placed on cellulose pads (25 mm) soaked in 650 μl of nutritive broth (depending of the bacteria of interest, different nutritive broth can be used) supplemented with 0.5% pyruvate or catalase (protect against oxygen toxic effect) and KDO-N$_3$ (4 mM) in Petri dishes. Petri dishes containing the samples were incubated at 37° C. for a certain time, (depending the bacteria of interest).

Next, CuSO$_4$ and TGTA, at a final concentration of 2 mM and 4 mM respectively, were mixed overnight in a phosphate buffer (0.05 M, pH 7.5) at 37° C. under vigorous shaking. Next, aminoguanidine, sodium ascorbate and A488-yne at final concentrations of 4 mM, 5 mM and 0.13 mM respectively were added to CuSO$_4$/TGTA overnight mix.

Finally, individual membranes were placed on cellulose pads soaked in 650 μl of this solution in Petri dishes and incubated at room temperature for 30 minutes.

Images were recorded with epifluorescence automated microscope (Nikon TE2000-E-PFS, Nikon, France) equipped with a CoolSNAP HQ 2 camera (Roper Scientific, Roper Scientific SARL, France) and a 100×/1.4 DLL objective. Excitation light was emitted by a 120 W metal halide light and signal was monitored using appropriate filters. Digital analysis and image processing were conducted by a custom automation script (Visual Basic) under Metamorph 7.5 (Molecular Devices, Molecular Devices France, France), as previously described [50,51].

5. In conclusion, it has been demonstrated that the KDO analogue can be metabolically assimilated and incorporated into the LPS without the necessity to use genetically modified bacteria. More interestingly the fact that the modified KDO needs first to be metabolically assimilated led to the use of this method for fast detection (the overall process taking less than one day) of metabolically active/viable Gram negative bacteria. This last application is very powerful in regard to the fact that detection of viable bacteria needs normally between 2 days and more than one month depending on the bacterial strain.

Severe pathogens are hiding amongst Gram negative bacteria, and the rapid identification of viable cells represents a major sanitary challenge. The present invention therefore provides a simple strategy to label the cell surface of metabolically active Gram negative bacteria, via metabolic incorporation of a modified ulosonic acid or ulosonate residue such as KDO into their lipopolysaccharide, followed by further conjugation using click-chemistry.

Of course, KDO-N₃ assimilation can be subsequently coupled to the fluorescence in situ hybridization (FISH) [24] or any other well-known procedure allowing the specific detection of viable bacteria of interest.

The ribosomal-RNA (rRNA) approach to microbial evolution and ecology has become an integral part of environmental microbiology. Based on the patchy conservation of rRNA, oligonucleotide probes can be designed with specificities that range from the species level to the level of phyla or even domains. When these probes are labelled for instance with fluorescent dyes or the enzyme horseradish peroxidase, they can be used to identify single microbial cells directly by fluorescence in situ hybridization (FISH) [38]. A new approach has been proposed using specifically phage [39].

EXAMPLE 2

Assimilation of 8-O-(4-ethynylbenzyl)-3-deoxy-D-manno-octulosonic Acid (KDO-CCH)

This compound 8-O-(4-ethynylbenzyl)-3-deoxy-D-manno-octulosonic acid or its salt (8-O-(4-ethynylbenzyl)-3-deoxy-D-manno-octulosonate), analog of compound (Ia-1) can be prepared by the following process:

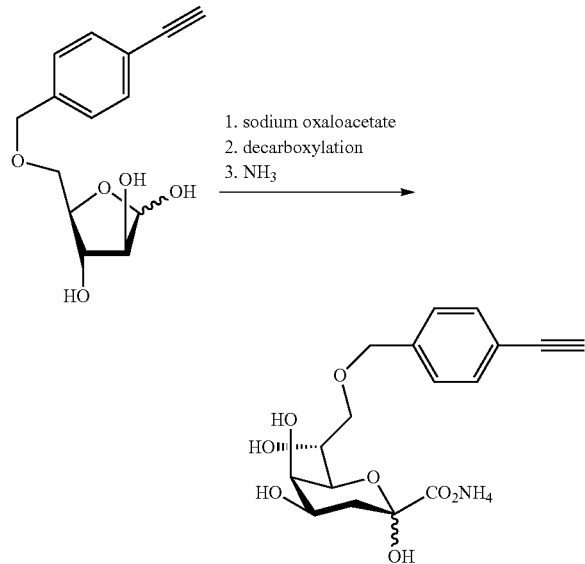

A cool solution of 5-O-(4-ethynylbenzyl)-D-arabinofuranose in water can be added to a solution of oxaloacetic acid in water, the pH of which being adjusted to ~10.5-11 by addition of aqueous NaOH. After being stirred at room temperature, the solution can be neutralized, and shortly heated at 80° C.

After its pH being adjusted to ~7 with AcOH, the mixture can purified by anion exchange chromatography on formate resin. After initial elution with water, further elution with a concentration gradient of formic acid, freeze-drying, treatment with an acidic resin, neutralization by ammonia, and concentration, can give ammonium 8-O-(4-ethynylbenzyl)-3-deoxy-D-man no-octulosonate.

The incorporation of the compound in the bacterial LPS and the labeling can be then carried out with an azido-derived labeling molecule, using the same reagents and methods as for KDO-N₃ (example 1).

KDO-CCH (before neutralization by ammonia):

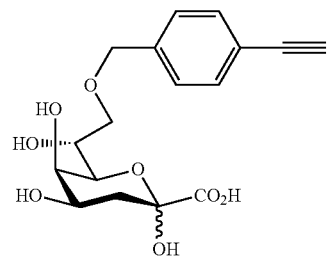

EXAMPLE 3

Assimilation of 9-azido-5,7-diacetamido-3,5,7,9-tetradeoxy-D-glycero-D-talo-non-2-ulosonic Acid and Specific Detection of *Legionella* Bacteria This compound 9-azido-5,7-diacetamido-3,5,7,9-tetradeoxy-D-glycero-D-talo-non-2-ulosonic acid or its salt (9-azido-5,7-diacetamido-3,5,7,9-tetradeoxy-D-glycero-D-talo-non-2-ulosonate), analog of compound (Ib-1) can be prepared by the following process [52]:

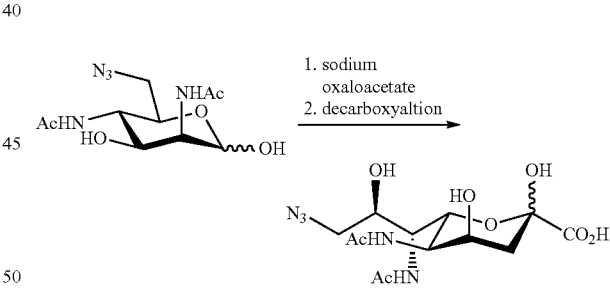

6-azido-2,4-diacetamido-2,4,6-trideoxy-D-mannopyranose can be added to a solution of oxaloacetic acid in water, the pH of which being adjusted to ~10.5-11 by addition of aqueous NaOH, and the mixture being stirred at room temperature in the presence or not of sodium tetraborate. Further additions of oxaloacetic acid might be necessary to ensure a good conversion. After neutralization with an acidic resin, filtration and concentration to a small volume, the solution could be applied to a formate resin, washed with water, and eluted with formic acid. Further purification, for example by reversed-phase HPLC, might be necessary.

The incorporation of the compound in the bacterial LPS and the labeling can be then carried out with the same reactive groups, the same reagents and methods as for KDO (example 1).

EXAMPLE 4

Assimilation of 5,7-diazidoacetamido-3,5,7,9-tetradeoxy-D-glycero-D-talo-non-2-ulosonic Acid and Specific Detection of *Legionella* Bacteria This compound 5,7-diazidoacetamido-3,5,7,9-tetradeoxy-D-glycero-D-talo-non-2-ulosonic acid or its salt (5,7-diazidoacetamido-3,5,7,9-tetradeoxy-D-glycero-D-talo-non-2-ulosonate), analog of compound (Ib-1), can be prepared like in the previous example 2, by reaction of 2,4-diazidoacetamido-2,4,6-trideoxy-D-mannopyranose with oxaloacetic acid.

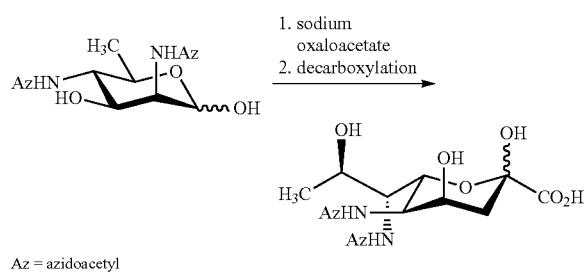

Az = azidoacetyl

The incorporation of the compound in the bacterial LPS and the labeling thereof can be then carried out as for KDO.

EXAMPLE 5

Use of Various Culture Media

The kind of culture medium is not limitative as both M9 and LB *E. coli* culture media have been successfully tested.

1) Materials and Methods
1.1) Bacterial Strains and Growth Conditions

*E. coli* K12 wild type strain grown in M9 medium (containing also: casamino acid 0.2%, glucose 0.2%, CaCl2 1 mM, MgSO4 5 mM) or in Luria-Bertani (LB) medium [54]. Cells were grown in a rotary shaker (200 rpm) at 37° C.

1.2) Copper Catalysed Click Chemistry

Overnight cultures were diluted 100 times in fresh medium (final volume 200 µl) containing KDO-N3 (1 mM). Bacteria were incubated at 37° C. for 12 hours and then washed 3 times with phosphate buffer (0.05 M, pH 7.5) by centrifugation at 14000×g for 2 min at room temperature.

A click pre-mix composed of CuSO4 and TGTA, at a final concentration of 2 mM and 4 mM respectively, is incubated overnight in a phosphate buffer (0.05 M, pH 7.5) at 37° C. under vigorous shaking. Next, amino guanidine, sodium ascorbate and A488-yne at final concentrations of 4 mM, 5 mM and 0.13 mM respectively were added to the overnight click pre-mix. Bacteria were then re-suspended in this solution and incubated 30 minutes at 37° C. under shaking. Finally, cells were washed 3 times with phosphate buffer by centrifugation at 14000× g for 2 min at room temperature.

1.3) Fluorescence Microscopy

Microscopic analysis were performed after Copper click chemistry on bacterial inoculum placed onto glass cover slips and covered with a thin (1 mm thick) semisolid 1% agar pad made with dilute LB (1/10 in phosphate buffer). Images were recorded with an epifluorescence automated microscope (Nikon TE2000-E-PFS, Nikon, France) equipped with a Cool SNAP HQ 2 camera (Roper Scientific, Roper Scientific SARL, France) and a 100×/1.4 DLL objective. Excitation light was emitted by a 120 W metal halide light and signal was monitored using appropriate filters. Digital analysis and image processing were conducted by a custom automation script (Visual Basic) under Metamorph 7.5 (Molecular Devices, Molecular Devices France, France).

2) Results

KDO assimilation occurs whatever the culture medium used.

Analysis has been performed on 616 *E. coli* cells from LB medium and 598 *E. coli* cells from minimum medium (M9).

A higher KDO assimilation is obtained when cells were grown in LB medium compared to M9 medium. However, both media are convenient and sufficient to detect and quantify cultivable bacteria.

EXAMPLE 6

Detection and Counting of Cultivable/Living and Dead *E. coli* Cells

Known numbers of both cultivable *E. coli* capable of multiplying and dead *E. coli* have been contacted with KDO-N3. KDO-N3 was incorporated only in living *E. coli*. KDO-N3 was incorporated in all of the living *E. coli*.

1) Materials and Methods
1.1) Bacterial Strains and Growth Conditions

*E. coli* K12 was grown in Luria-Bertani (LB) medium in a rotary shaker (200 rpm) at 37° C. Dead *E. coli*—K12 were obtained after heating at 120° C. for 15 minutes.

1.2) Copper Catalysed Click Chemistry (as Disclosed in Example 5).

1.3) Bacterial Counting and Fluorescence Microscopy 1.3.1) For total bacterial scoring, cells were fixed and stained in a solution of paraformaldehyde 3%—DAPI 2 µg/ml and filtered on an isopore polycarbonate membrane (Milipore).

1.3.2) Colony forming units (CFU) were also monitored by plating dilutions before Copper click chemistry.

1.3.3) Microscopic analyses were performed after Copper click chemistry on bacterial inoculum placed onto glass cover slips and covered with a thin (1 mm thick) semisolid 1% agar pad made with dilute LB (1/10 in phosphate buffer). Images were recorded with an epifluorescence automated microscope (Nikon TE2000-E-PFS, Nikon, France) equipped with a Cool SNAP HQ 2 camera (Roper Scientific, Roper Scientific SARL, France) and a 100×/1.4 DLL objective. Excitation light was emitted by a 120 W metal halide light and signal was monitored using appropriate filters. Digital analysis and image processing were conducted by a custom automation script (Visual Basic) under Metamorph 7.5 (Molecular Devices, Molecular Devices France, France).

2) Results 2.1) the total cell concentration calculated by the total scoring disclosed in 1.3.1) was $9 \cdot 10^9 +/- 0.1 \cdot 10^9$ cells/ml while the cultivable cell concentration counted by the colonies counting disclosed in 1.3.2) was $4 \cdot 10^9 +/- 0.15 \cdot 10^9$ cfu/ml. These result indicates that 44.5% (+/−4%) of all cells present in this sample are cultivable.

2.2) the counting by fluorescence after click chemistry as disclosed in paragraphs 1.2/1.3.3) provided the following results. One Sample was incubated without KDO-N3, and one sample was incubated with KDO-N3. Fluorescence analysis has been performed on 1878 *E. coli* cells with KDO-N3 and 3039 *E. Coli* cells without KDO-N3. It enabled to determine a threshold of arbitrary fluorescence unit of 30 below which the cells are dead and above which the cells are cultivable. Next, applying this threshold (30), it was possible to count cell identified as dead (below 30) and identified as cultivable (above 30) on bacteria having reacted through click chemistry as in 1.3.3) Doing this evaluation, 1587 dead cells (KDO-N3−) and 1452 cultivable cells (KDO-N3+) leading to a 47.7% of cultivable cell were found. This value appears statistically identical to the one obtained using dead and cultivable cells, 44.5% demonstrating that only cultivable cells are detected by the method of the present invention.

EXAMPLE 7

Detection of Only Gram-Cultivable Cells

A mixture of Gram+ bacteria (*B. subtilis*) and Gram− bacteria (*E. Coli*) have been contacted with KDO-N3. Only cultivable Gram− bacteria was labeled with KDO-N3 and detected.

1) Material and Method 1.1) Bacterial Strains and Growth Conditions

*E. coli* K12 wild type strain rendered fluorescent via m-cherry [55], *E. coli* K12 sodA-mCherry [55] and *B. subtilis* were grown in Luria-Bertani (LB) medium in a rotary shaker (200 rpm) at 37° C.

1.2) Copper Catalysed Click Chemistry (as Disclosed in Example 6)

1.3) Bacterial Counting and Fluorescence Microscopy (as Disclosed in Example 5)

2) Results

*B. subtilis* and *E. coli* were grown in LB medium during 12 hours. After that time cultivable cell concentration from *E. coli* ($1.66 \cdot 10^9$ cfu/ml) and *B. subtilis* ($5.9 \cdot 10^8$ cfu/ml) have been identified by counting disclosed in paragraph 1.32), indicating that 26% of the cultivable cells were *B. subtilis* and 74% were *E. coli*.

Moreover, because an *E. coli* sodA-mCherry strain was used, it was possible to differentiate *E. coli* and *B. subtilis* using fluorescence as disclosed above but before click chemistry. Among the 696 analyzed cells, 170 were mCherry negative (24.4%) representing by consequence *B. subtilis*, and 526 mCherry positive (75.6%) representing by consequence *E. coli*. These results are confirmed with the percentages obtained from the cfu values.

Then, all of the bacteria of the same sample have been subjected to the above click chemistry reaction and the results of counting via fluorescence are given in the following table 1.

Within the KDO-N3 negative cells, the number of mCherry negative cells representing by consequence *B. subtilis* (166) and the number of mCherry positive cells representing by consequence the number of *E. coli* cells (9) were evaluated. Within the KDO-N3 positive cells, the number of mCherry negative cells representing by consequence the number of *B. subtilis* (4) and the number of mCherry positive cells representing by consequence the number of cultivable *E. coli* (517) have been evaluated.

Using all these values, it was possible to identify 4 *B. subtilis* as false positive (about 2%). By contrasts the 9 *E. coli* KDO negative (about 2%) can be either false positive or false negative since the standard method error range is about 10%.

|  | KDO-N3+ | KDO-N3− | Total |
|---|---|---|---|
| mCherry + (*E. coli*) | 517 | 9 | 526 |
| mCherry − (*B. subtilis*) | 4 | 166 | 170 |
| Total | 521 | 175 | 696 |

These above results demonstrate therefore that KDO-N3 has well been assimilated in substantially only cultivable *E. coli* cells and not in cultivable *B. subtilis* cells.

EXAMPLE 8

Detection Via Biotin-Alkyne

After Kdo-N3 assimilation, click chemistry has been performed using biotin-alkyn and viable *E. coli* cells were detected using an anti-biotin antibody coupled to fluorochome Alexa Fluor A494. As observed by comparing cultivable counting and Kdo positive cell counting, all viable *E. coli* bacteria were detected by the following experimental procedure.

1) Bacterial Strains and Growth Conditions

*E. coli* K12 wild type strain is grown in Luria-Bertani (LB) medium in a rotary shaker (200 rpm) at 37° C.

2) Copper Catalyzed Click Chemistry:

Overnight cultures were diluted 100 times in fresh medium (final volume 200 μl) containing KDO-N3 (1 mM). Bacteria were incubated at 37° C. for 12 hours, washed 3 times with phosphate buffer (0.05 M, pH 7.5) by centrifugation at 14000×g for 2 min at room temperature. A click pre-mix composed of CuSO4 and TGTA, at a final concentration of 2 mM and 4 mM respectively, was incubated overnight in phosphate buffer at 37° C. under vigorous shaking. Next, aminoguanidine, sodium ascorbate at final concentrations of 4 mM and 5 mM respectively were added to the overnight pre-mix click. This "click-mix" was added to the washed culture and supplemented or not with biotin-alkyn (Carbosynth) (1 to 100 μg) and incubated for 1 to 60 min at 37° C. under shaking.

3) Bacterial Counting and Fluorescence Microscopy:

For total bacterial scoring both before and after the Copper click chemistry, cells were fixed and stained in a solution of paraformaldehyde 3%—DAPI 2 μg/ml and filtered on an isopore polycarbonate membrane (Milipore).

An anti-biotin antibody coupled to Alexa Fluor A594 (Jackson Immuno Research) was used diluted 10 to 1000 times to label bacteria. Colony forming units (CFU) were also monitored by plating dilutions before Copper click chemistry.

Microscopic analyses were performed after Copper click chemistry on bacterial inoculum placed onto glass cover slips and covered with a thin (1 mm thick) semisolid 1% agar pad made with dilute LB (1/10 in phosphate buffer). Images were recorded with an epifluorescence automated microscope (Nikon TE2000-E-PFS, Nikon, France) equipped with a CoolSNAP HQ 2 camera (Roper Scientific, Roper Scientific SARL, France) and a 100×/1.4 DLL objective. Excitation light was emitted by a 120 W metal halide light and signal was monitored using appropriate filters. Digital analysis and image processing were conducted by a custom automation script (Visual Basic) under Metamorph 7.5 (Molecular Devices, Molecular Devices France, France).

BIBLIOGRAPHY

[1] E. Sletten, C. R. Bertozzi, *Acc. Chem. Res.* 2011, in press, DOI: 10.1021/ar200148z; M. Boyce, C. R. Bertozzi, *Nature methods* 2011, 8, 638-642; D. H. Dube, K. Champasa, B. Wang, *Chem. Commun.* 2011, 47, 87-101; S. T. Laughlin, C. R. Bertozzi, *Proc. Natl. Acad. Sci. USA* 2009, 106, 12-17; J. Du, M. A. Meledeo, Z. Wang, H. S. Khanna, V. D. P. Paruchuri, K. J. Yarema, *Glycobiology* 2009, 19, 1382-1401; S. R. Hanson, W. A. Greensberg, C.-H. Wong, *QSAR Comb. Sci.* 2007, 26, 1243-1253.

[2] L. Yang, J. O, Nyalwidhe, S. Guo, R. R. Drake, O. J. Semmes, *Mol. Cell. Proteomics* 2011, 10, M110.007294.

[3] For an application to yeast glycans, see: M. A. Breidenbach, J. E. G. Gallagher, D. S. King, B. P. Smart, P. Wu, C. R. Bertozzi, *Proc. Natl. Acad. Sci. USA,* 2010, 107, 3988-3993.

[4] W. Yi, X. Liu, Y. Li, J. Li, C. Xia, G. Zhou, W. Zhang, W. Zhao, X. Chen, P. G. Wang, *Proc. Natl. Acad. Sci. USA,* 2009, 106, 4207-4212.

[5] see for example: G. Samuel, J.-P. Hogbin, L. Wang, P. R. Reeves, *J. Bacteriol.* 2004, 186, 6536-6543; B. Ma, J. L. Simala-Grant, D. E. Taylor, *Glycobiology* 2006, 16, 158R-184R.

[6] Exogenous L-Fucose is actually metabolized into L-lactate or L-1,2-propanediol, which could potentially prove a source of dissemination of the chemical reporter into various metabolites. See: L. Baldomà, J. Aguilar, *J. Bacteriol.* 1988, 170, 416-421

[7] L. Cipolla, L. Gabrielli, D. Bini, L. Russo, N. Shaikh, *Nat. Prod. Rep.,* 2010, 27, 1618-1629.

[8] A viable *E. coli* strain lacking KDO as however been recently described. See: T. C. Meredith, P. Aggawal, U. Mamat, B. Lindner, R. W. Woodward, *ACS Chem. Biol.* 2006, 1, 33-42.

[9] O. Hoist, *FEMS Microbiol. Lett.* 2007, 271, 3-11.

[10] L. Cipolla, A. Polissi, C. Airoldi, P. Galliani, P. Sperandeo, F. Nicotra, *Curr. Drug. Discov. Technol.* 2009, 6, 19-33.

[11] J. O. Capobianco, R. P. Darveau, R. C. Goldman, P. A. Lartey, A. G. Pernet, *J. Baceriol.* 1987, 169, 4030-4035.

[12] C. W. Tornøe, C. Christensen, M. Meldal, *J. Org. Chem.* 2002, 67, 3057-3064; V. V. Rostovtsev, L. G. Green, V. V. Fokin, K. B. Sharpless, *Angew. Chem. Int. Ed.* 2002, 41, 2596-2599.

[13] For a review, see: A. Banaszek, J. Mlynarski in *Studies in Natural Products Chemistry, Vol.* 30 (Ed.: Atta-ur-Rahman), Elsevier, Amsterdam, 2005, pp. 419-482.

[14] In the course of this work, a very similar access to 8-azido-8-deoxy-KDO was published: R. Winzar, J. Philips, M. J. Kiefel, *Synlett* 2010, 583-586.

[15] M. A. Ghalambor, E. C. Heath, *Biochem. Biophys. Res. Commun.* 1963, 11, 288-293.

[16] I. A. Smellie, S. Bhakta, E. Sim, A. J. Fairbanks, *Org. Biomol. Chem.* 2007 5, 2257-2266.

[17] S. Müller-Loennies, B. Lindner, H. Brade. *J. Biol. Chem.,* 2003, 278, 34090-34101.

[18] V. Hong, N. S. Steinmetz, M. Manchester, M. G. Finn, *Bioconj. Chem.* 2010, 21, 1912-1916.

[19] A. Baron, Y. Blériot, M. Sollogoub, B. Vauzeilles, *Org. Biomol. Chem.* 2008, 6, 1898-1901.

[20] J. A. May, A. C. Sartorelli, *J. Med. Chem.* 1979, 22, 971-976.

[21] E. Vinogradov, A. Korenevsky, T. J. Beveridge, *Carbohydr. Res.* 2003, 338, 1991-1997; S. Leone, A. Molinaro, C. De Castro, A. Baler, E. L. Nazarenko, R. Lanzetta, M. Parrilli, *J. Nat. Prod.* 2007, 70, 1624-1627.

[22] D. C. Ellwood, *J. Gen. Microbiol.* 1970, 60, 373-380.

[23] B. L. Ridley, B. S. Jeyaretnam, R. W. Carlson, *Glycobiology* 2000, 10, 1013-1023.

[24] M. Wagner, P. H. Nielsen, A. Loy, J. L. Nielsen, H. Daims, *Curr. Opin. Biotechnol.* 2006, 17, 83-91.

[25] Rahman, I., Shahamat, M., Kirchman, P. A., Russek-Cohen, E. and Colwell, R. R. (1994) Methionine uptake and cytopathogenicity of viable but nonculturable *Shigella dysenteriae* type 1. Appl. Environ. Microbiol. 60, 3573-3578.

[26] Nwoguh, C. E., Harwood, C. R. and Barer, M. R. (1995) Detection of induced L-galactosidase activity in individual nonculturable cells of pathogenic bacteria by quantitative cytological assay. Mol. Biol. 17, 545-554.

[27] Kogure, K., Simidu, U. and Taga, N. (1979) A tentative direct microscopic method for counting living marine bacteria. Can. J. Microbiol. 25, 415-420.

[28] Rodriguez, G. G., Phipps, D., Ishiguro, K. and Ridgeway, H. F. (1992) Use of a £uorescent redox probe for direct visualization of actively respiring bacteria. Appl. Environ. Microbiol. 58, 1801-1808.

[29] Thom, S. M., Horobin, R. W., Seidler, E. and Barer, M. R. (1993) Factors aiecting the selection and use of tetrazolium salts as cytochemical indicators of microbial viability and activity. J. Appl. Bacteriol. 74, 433-443.

[30] Ullrich, S., Karrasch, B., Hoppe, H.-G., Jeskulke, K. and Mehrens, M. (1996) Toxic eiects on bacterial metabolism of the redox dye 5-cyano-2,3-ditolyl tetrazolium chloride. Appl. Environ. Microbiol. 62, 4587-4593.

[31] Korgaonkar, K. S. and Ranade, S. S. (1966) Evaluation of acridine orange £uorescence test in viability studies of *Escherichia coli*. Can. J. Microbiol. 12, 185-190.

[32] Porter, K. G. and Feig, Y. S. (1980) The use of DAPI for identifying and counting aquatic micro£ora. Limnol. Oceanogr. 25, 943-948.

[33] Davey, H. M. and Kell, D. B. (1996) Flow cytometry and cell sorting of heterogeneous microbial populations: the importance of single-cell analyses. Microbiol. Rev. 60, 641-696.

[34] Parthuisot, N., Catala P., Lemarchand, K., Baudart, J., and Lebaron, P. (2000) Evaluation of ChemChrome V6 for bacterial viability assessment in waters. J. Appl Microbiol. 89, 370-380.

[35] Breeuwer, P., and Abee, T. (2000) Assessment of viability of microorganisms employing fluorescence techniques. Int. J. Food Microbiol. 10, 193-200.

[36] Berney, M., Vital, M., Hulshoff, I., Weilenmann, H U, Egli, T., and Hammes, F. (2008) Rapid, cultivation-independent assessment of microbial viability in drinking water. Water Res. 4é, 4010-4018.

[37] Rijpens, N P, and Herman, L M. (2002) J AOAC Int, 85, 984-995.

[40] Cuny, C., Lesbats, M., and Dukan, S. (2007) Induction of a global stress response during the first step of *Escherichia coli* plate growth. Appl. Environ. Microbiol. 73, 885-889.

[38] Amman, R. and Fuchs, B. M. Single-cell identification in microbial communities by improved fluorescence in situ hybridization techniques (2008) Nature Reviews Microbiology, 6, 339-348.

[39] Wu, L, Huang, T., Yang L, Pan, J., Zhu, S., and Yan X. (2011) Sensitive and selective bacterial detection using tetracysteine-tagged phages in conjunction with biarsenical dye. Angew Chem Int Ed Engl. 50, 5873-5877.

[41] Mackey, B. M., and Seymour, D. A. (1987) The effect of catalase on recovery of heat-injured DNA-repair mutants of *Escherichia coli*. J. Gen. Microbiol. 133, 1601-1610.

[42] Marthi, B., Shaffer, B. T., Lighthart, B., and Ganio, L. (1991) Resuscitation effects of catalase on airborne bacteria. Appl. Environ. Microbiol. 57, 2775-2776.

[43] McDonald, L. C., Hackney, C. R. and Ray, B. (1983) Enhanced recovery of injured *Escherichia coli* by compounds that degrade hydrogen peroxide or block its formation. Appl. Environ. Microbiol. 45, 360-365.

[44] Dukan, S., Belkin, S, and Touati D. (1999) Reactive oxygen species are partially involved in the bacteriocidal action of hypochlorous acid. Arch. Biochem. Biophys. 367, 311-316.

[45] Dukan, S., and Nystrom, T. (1999) Oxidative stress defense and deterioration of growth-arrested *Escherichia coli* cells. J. Biol. Chem. 274, 26027-26032.

[46] Ohtomo, R., and Saito, M. (2001) Increase in the culturable cell number of *Escherichia coli* during recovery from saline stress: possible implication for resuscitation from the VBNC state. Microb. Ecol. 42, 208-214.

[47] Ray, B., Jezeski, J. J., and Busta, F. F. (1971) Effect of rehydration on recovery, repair, and growth of injured freeze-dried *Salmonella anatum*. Appl. Microbiol. 22, 184-189.

[48] Speck, M. L., Ray, B., and Read, R. B. Jr. (1975) Repair and enumeration of injured coliforms by a plating procedure. Appl. Microbiol. 29, 549-550.

[49] Bogosian, G., and Bourneuf E. V. (2001) A matter of bacterial life and death. EMBO Rep. 2:770-774.

[50] I. A. Smellie, S. Bhakta, E. Sim, A. J. Fairbanks, *Org. Biomol. Chem.* 2007 5, 2257-2266.

[51] A. Ducret, E. Maisonneuve, P. Notareschi, A. Grossi, T. Mignot, S. Dukan, *PLoS One*, 2009, 4, e7282.

[52] Y. E. Tsvetkov, A. S. Shashkov, Y. A. Knirel, U. Zähringer, *Carbohydr. Res.* 2001, 335, 221-243.

[53] Valentin O. Rodionov, Stanislav I. Presolski, Sean Gardinier, Yeon-Hee Lim, and M. G. Finn, *J. Am. Chem. Soc.*, 2007, 129, 12696-12704.

[54] Bachmann B J (1987) Derivations and genotypes of some mutant derivatives of *Escherichia coli* K-12. *Escherichia coli* and *Salmonella typhimurium*: Cellular and Molecular Biology (Neidhardt F C, Ingraham J L, Low K B, Magasanik B, Schaechter M & Umbarger H E, eds), pp. 1190-1219. American Society for Microbiology, Washington, D.C.

[55] A. Ducret, E. Maisonneuve, P. Notareschi, A. Grossi, T. Mignot and S. Dukan (2009) A microscope automated fluidic system to study bacterial processes in real time. *PLoS One.* 2009 Sep. 30; 4(9):e7282.

The invention claimed is:

1. A method for labeling specifically living bacteria of a given category of bacteria in a sample comprising bacteria, the method comprising the steps of:
    a) incubating said bacteria of said sample with at least one analog of a monosaccharide compound, said monosaccharide being an endogenous monosaccharide residue of glycans of the outer membrane of the given category of bacteria, the endogenous monosaccharide residue comprising an ulosonic acid or ulosonate salt residue, the analog of a monosaccharide compound being a modified monosaccharide substituted at a given position by a first reactive group capable of reacting with a second reactive group of a labeling molecule,
    b) contacting said bacteria with a labeling molecule comprising a second reactive group, for generating the reaction of said first reactive group of said analog residue incorporated within said glycans of the outer membrane of said living bacteria with said second reactive group of said labeling molecule.

2. The method according to claim 1 for labeling specifically bacteria capable of multiplying wherein said bacteria are incubated in a culture medium in or on which said bacteria are capable of multiplying.

3. The method according to claim 1, comprising a further step c) of:
    detecting living bacteria in detecting whether said bacteria comprise said labeling molecule bound to the glycans of their outer membrane and/or immobilizing said living bacteria bearing said labeling molecule onto a solid substrate.

4. The method according to claim 3 wherein said labeling molecule is a detectable molecule comprising a detectable substance or capable of reacting with, or being bound to, a detectable substance, or said labeling molecule is a first molecule bearing a second reactive group, said first molecule being capable of reacting with, or being bound to, at least one of a second molecule and a solid substrate.

5. The method according to claim 4 for specifically detecting living bacteria of a given category of bacteria in a sample comprising bacteria, wherein said labeling molecule is a detectable molecule comprising a detectable substance, the method comprising the step c) of detecting living bacteria in detecting whether said bacteria comprise said detectable molecule bound to the glycans of their outer membrane.

6. The method according to claim 4 wherein said labeling molecule is a first ligand or first binding protein bearing a second reactive group, and in step c) said living bacteria coupled to said first ligand or first binding protein is detected and/or immobilized by contacting said first ligand or first binding protein with a second ligand or second binding protein reacting or binding specifically to said first ligand or first binding protein.

7. The method according to claim 6 wherein said labeling molecule is a first ligand, bearing said second reactive group, and in step c) said living bacteria coupled to said first ligand are detected by reaction of said bacteria with an antibody specific to said first ligand, said antibody bearing a detectable substance.

8. The method according to claim 4 wherein the detectable substance is a fluorochrome or luminescent molecule detectable by fluorescence or luminescence.

9. The method according to claim 1 wherein the analog of monosaccharide compound is an ulosonic acid having one of the following formulas (I) or (II), or an ulosonate salt thereof:

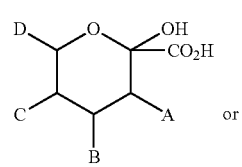

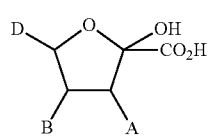

wherein
A, B, and C is independently H, OH, NH$_2$, OH, and NH$_2$ being unsubstituted or substituted by a protecting group, and D is an alkyl chain in C$_2$ to C$_4$, each carbon being unsubstituted or substituted by OH or NH$_2$, unsubstituted or substituted by a protecting group, and at least one of A, B, C, or D groups is substituted by said first reactive group.

10. The method according to claim 1 wherein the analog of monosaccharide is a substituted octulosonic acid, or octulosonate salt compound, or a substituted nonulosonic acid, or nonulosonate salt compound.

11. The method according to claim 10 for detecting specifically living Gram negative bacteria wherein the given category of bacteria is the category of the Gram negative bacteria and said endogenous monosaccharide residue of a lipopolysaccharide layer of the outer membrane of the bacteria is a deoxyoctulosonic acid or deoxyoctulosonate residue, and said analog of monosaccharide compound is a substituted deoxyoctulosonic acid or deoxyoctulosonate compound.

12. The method according to claim 11 wherein the analog of deoxyoctulosonic acid or deoxyoctulosonate compound is substituted by said reactive group at one position selected among the positions 3, 4, 5, 7, and 8 of the monosaccharide.

13. The method according to claim 12 wherein the analog of deoxyoctulosonic acid or deoxyoctulosonate compound of formula (I) or (II) is substituted by said first reactive group R$_1$ at the position 8 wherein D=-CHOH—CH$_2$—R$_1$, A=H, B=OH, C=OH in formula (I) or D=-CHOH—CHOH—CH$_2$—R$_1$, A=H, B=OH in formula (II).

14. The method according to claim 11 wherein the Gram negative bacteria comprise E. coli, Salmonella typhimurium, Legionella pneumophila, and Pseudomonas aeruginosa.

15. The method according to claim 1 for labeling specifically living Legionella pneumophila bacteria and the given category of bacteria is the category of the Legionella pneumophila bacteria, and said endogenous monosaccharide residue of said lipopolysaccharide layer of the outer membrane of the bacteria is a 4-epilegionaminic acid (5,7-diamino-3,5,7,9-tetradeoxy-D-glycero-D-talo-non-2-ulosonic acid) or 4-epilegionaminate residue, or a legionaminic acid (5,7-diamino-3,5,7,9-tetradeoxy-D-glycero-D-galacto-non-2-ulosonic acid) or legionaminate residue, and the analog of a monosaccharide compound is, respectively, a substituted 4-epilegionaminic acid or 4-epi-legionaminate compound, or a substituted legionaminic acid or legionaminate compound, substituted at one position selected among the positions 3, 4, 5, 7, 8, and 9 of the monosaccharide cycle.

16. The method according to claim 1 for labeling, specifically living Pseudomonas aeruginosa bacteria and the said given category of bacteria is the category of the Pseudomonas aeruginosa bacteria and said endogenous monosaccharide residue of said lipopolysaccharide layer of the outer membrane of the bacteria is a 8-epilegionaminic acid (5,7-diamino-3,5,7,9-tetradeoxy-L-glycero-D-galacto-non-2-ulosonic acid) or 8-epilegionaminate residue, or a pseudaminic acid (5,7-diamino-3,5,7,9-tetradeoxy-L-glycero-L-manno-non-2-ulosonic acid) or pseudaminate residue, and the analog of a monosaccharide compound is, respectively, a substituted 8-epilegionaminic acid or 8-epilegionaminate compound, or a substituted pseudaminic acid or pseudaminate compound.

17. The method according to claim 1 wherein the first reactive group is selected among groups consisting of or bearing the group azido, and groups consisting of or bearing the group alkyne, and the second reactive group is selected among groups consisting of or bearing, respectively, the groups alkyne and azido, and reacting the azido reactive group with the alkyne reactive group is carried out in performing an azide alkyne cycloaddition.

18. The method according to claim 17 wherein the reaction is carried out in copper catalyzed conditions in the presence of a tris-triazolyl ligand.

19. The method according to claim 2 for numbering living bacteria wherein the incubation of step a) and reaction of step b) are carried out on a solid substrate, so that the cultivated bacteria emanating from a same original bacterium, which has been multiplied, are grouped together and can be visualized with a microscope and the detectable molecule can be detected by visualization with said microscope.

20. A method according to claim 1, further comprising providing a kit, wherein said kit comprises:
a said analog of a monosaccharide compound comprising an ulosonic acid or ulosonate compound substituted at a given position by a said first reactive chemical group, and a said labeling molecule comprising a said second reactive group capable of reacting with said first reactive group, and reactants for generating the reaction of said first reactive group of said analog residue incorporated within said glycans of the outer membrane of said bacteria with said second reactive group of said labeling molecule, and a culture or incubation medium allowing the growth of a said given category of bacteria, specific to the growth of said given category of bacteria.

21. A method according to claim 20, wherein the kit comprises:
a said detectable molecule comprising a said second reactive group capable of reacting with said first reactive group, and a solid medium allowing visualization of the bacteria after incubating with the said analog of a monosaccharide compound, said reactants and said detectable molecule.

22. A method according to claim 20, wherein the kit comprises:
a said analog of a monosaccharide compound being a deoxyoctulosonic acid or deoxyoctulosonate salt compound substituted by a said first reactive group comprising an azido or alkyne group, and a said second reactive group of the detectable molecule bearing an alkyne or, respectively, azido group, and said reactants comprising a copper catalyst and a tris-triazolyl ligand.

23. The method according to claim 1, wherein the given position is a position which comprises a free group in the endogenous monosaccharide residue incorporated within the glycans of the outer membrane of the bacteria.

24. The method according to claim 4, wherein the second molecule comprises a detectable substance and/or the second molecule is bound to the solid substrate.

25. The method according to claim 9, wherein the protecting group for A, B, C, and D is selected from the group consisting of alkyl, hydroxyalkyl, acyl, formyl and imidoyl.

26. The method according to claim 7, wherein the first ligand is biotin.

27. The method according to claim 15, wherein the substituted legionaminic acid or legionaminate compound is substituted at one position selected from the group consisting of position 3, position 4, position 5, position 7, position 8, and position 9.

28. The method according to claim 19, wherein the solid substrate is a membrane filter.

29. The method according to claim 4, wherein the given category of bacteria is the category of the *Pseudomonas aeruginosa* bacteria, and said endogenous monosaccharide residue of said lipopolysaccharide layer of the outer membrane of the bacteria is a 8-epilegionaminic acid (5,7-diamino-3,5,7,9-tetradeoxy-L-glycero-D-galacto-non-2-ulosonic acid) or 8-epilegionaminate residue, or a pseudaminic acid (5,7-diamino-3,5,7,9-tetradeoxy-L-glycero-L-manno-non-2-ulosonic acid) or pseudaminate residue, and the analog of a monosaccharide compound is, respectively, a substituted 8-epilegionaminic acid or 8-epilegionaminate compound, or a substituted pseudaminic acid or pseudaminate compound.

* * * * *